United States Patent [19]
Greenwald et al.

[11] Patent Number: 5,965,566
[45] Date of Patent: *Oct. 12, 1999

[54] HIGH MOLECULAR WEIGHT POLYMER-BASED PRODRUGS

[75] Inventors: Richard B. Greenwald, Somerset; Annapurna Pendri, Matawan; Hong Zhao, Piscataway, all of N.J.

[73] Assignee: Enzon, Inc., Piscataway, N.J.

[ * ] Notice: This patent is subject to a terminal disclaimer.

[21] Appl. No.: 08/914,927

[22] Filed: Aug. 20, 1997

Related U.S. Application Data

[63] Continuation-in-part of application No. 08/700,269, Aug. 20, 1996, Pat. No. 5,840,900, which is a continuation-in-part of application No. 08/537,207, Sep. 29, 1995, Pat. No. 5,880,131, which is a continuation-in-part of application No. 08/380,873, Jan. 30, 1995, Pat. No. 5,614,549, which is a continuation-in-part of application No. 08/140,346, Oct. 20, 1993, abandoned.

[51] Int. Cl.[6] .................. A61K 31/44; C07D 491/22
[52] U.S. Cl. .................. 514/279; 514/283; 514/449; 546/48; 546/51; 549/510; 549/511
[58] Field of Search .................. 514/279, 283, 514/449; 546/48, 51; 549/510, 511

[56] References Cited

U.S. PATENT DOCUMENTS

| | | | |
|---|---|---|---|
| 4,101,380 | 7/1978 | Rubinstein et al. | 195/83 |
| 4,179,337 | 12/1979 | Davis et al. | 435/181 |
| 4,275,000 | 6/1981 | Ross | 260/112 R |
| 4,534,699 | 8/1985 | Sears | 260/403 |
| 4,582,805 | 4/1986 | Bozzelli et al. | 435/180 |
| 4,680,338 | 7/1987 | Sundoro | 525/54.1 |
| 4,814,470 | 3/1989 | Colin et al. | 514/449 |
| 4,904,582 | 2/1990 | Tullis | 435/6 |
| 4,942,184 | 7/1990 | Haugwitz et al. | 544/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,091,176 | 2/1992 | Braatz et al. | 424/18.17 |
| 5,122,614 | 6/1992 | Zalipsky | 548/520 |
| 5,136,060 | 8/1992 | Holton | 549/510 |
| 5,157,049 | 10/1992 | Haugwitz et al. | 514/449 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,439,686 | 8/1995 | Desai et al. | 424/451 |
| 5,440,056 | 8/1995 | Klein et al. | 549/510 |
| 5,468,769 | 11/1995 | Klein et al. | 514/449 |
| 5,484,809 | 1/1996 | Hostetler et al. | 514/449 |
| 5,530,020 | 6/1996 | Gunawardana et al. | 514/449 |
| 5,602,141 | 2/1997 | Bedeschi et al. | 514/279 |
| 5,773,522 | 6/1998 | Angelucci et al. | 525/329.4 |

FOREIGN PATENT DOCUMENTS

| | | |
|---|---|---|
| 0510356 | 3/1992 | European Pat. Off. . |
| 0524093 | 7/1992 | European Pat. Off. . |
| WO 81/01145 | 4/1981 | WIPO . |
| 91/02763 | 3/1991 | WIPO . |
| WO 95/10304 | 4/1995 | WIPO . |

OTHER PUBLICATIONS

Nathan et al, "Polymer Preprints", vol. 31, pp. 213–214, 1990.
Zalipsky et al, Eur. Polym. J., vol. 19, No. 12, pp. 1177–1183 (1983).
Ouchi et al, Drug Design & Discovery, vol. 9, pp. 93–105, (1992).
Mathew et al, J. Med. Chem., 35, pp. 145–151 (1992).
Cecchi et al, J. Med. Chem., vol. 24, pp. 622–625 (1981).
Weiner et al, Journal of Medicinal Chemistry, vol. 16, NO. 5, (1973).
Nicolaou, Nature, vol. 364, pp. 464–466, 29 Jul. 1993.
Commercon et al, Tetrahedron Letters, vol. 33, No. 36, pp. 5158–5188 (1992).
Magre et al, J. Org. Chem., vol. 51, pp. 797–802 (1986).
Gueritte–Voegelein et al, J. Med Chem., 34, pp. 992–998 (1991).

*Primary Examiner*—Ba K. Trinh
*Attorney, Agent, or Firm*—Roberts & Mercanti, L.L.P.

[57] ABSTRACT

The present invention is directed compositions of the formula:

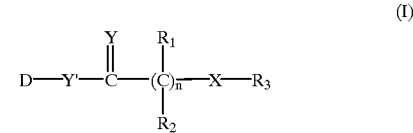

wherein:
D is a residue of biologically active moiety;
X is an electron withdrawing group;
Y and Y' are independently O or S;
(n) is zero (0) or a positive integer, preferably from 1 to about 12;
wherein: $R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;
wherein: $R_3$ is a substantially non-antigenic polymer, $C_{1-12}$ straight or branched alkyl or substituted allyl, $C_{5-8}$ cycloalkyl or substituted cycloalkyl, carboxyalkyl, carboalkoxy alkyl, dialkylaminoalkyl, phenylalkyl, phenylaryl or

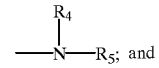

wherein: $R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring. In preferred embodiments, the prodrugs contain a polyethylene glycol having a molecular weight of at least about 20,000.

52 Claims, 17 Drawing Sheets

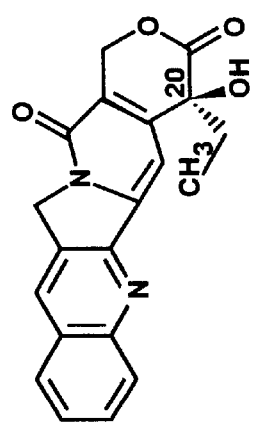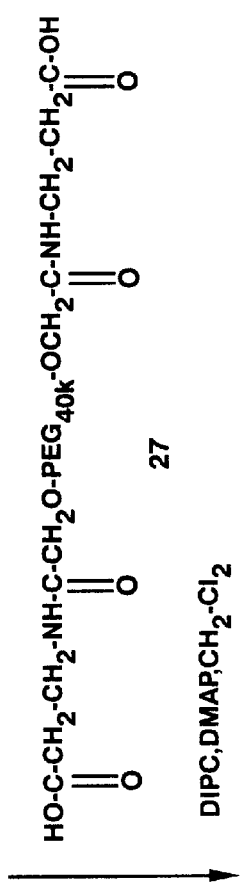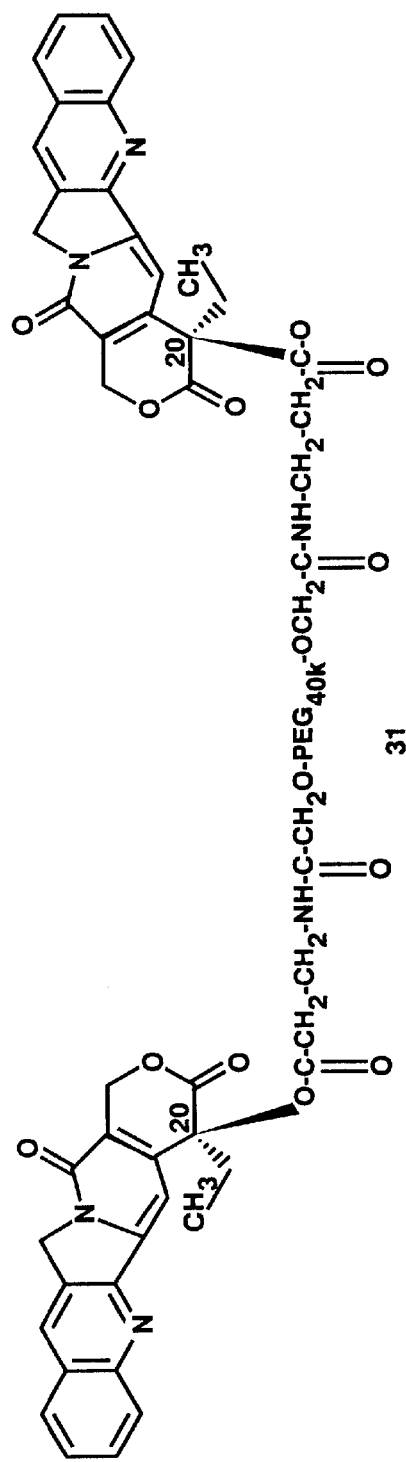
FIG-9

HIGH MOLECULAR WEIGHT POLYMER-BASED PRODRUGS

RELATED APPLICATIONS

This application is a continuation-in-part of U.S. patent application Ser. No. 08/700,269 filed Aug. 20, 1996, now U.S. Pat. No. 5,840,900 which, in turn, is a continuation-in-part of U.S. patent application Ser. No. 08/537,207 filed Sep. 29, 1995, now U.S. Pat. No. 5,880,131, which, in turn, is a continuation-in-part of U.S. patent application Ser. No. 08/380,873 filed Jan. 30, 1995, now U.S. Pat. No. 5,614,549 which, in turn, is a continuation-in-part of U.S. patent application Ser. No. 08/140,346 filed Oct. 20, 1993 now abandoned. The contents of each of the foregoing applications are incorporated herein by reference.

TECHNICAL FIELD

The present invention relates to water soluble prodrugs. In particular, the invention relates to the use of relatively high molecular weight non-antigenic polymers to prepare prodrugs.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal is either insoluble in aqueous fluids or is rapidly degraded in vivo. Alkaloids are often especially difficult to solubilize.

For example, several methods have been suggested to overcome the problems associated with administering paclitaxel, (also known as Taxol®, Bristol-Myers Squibb Co. NY, N.Y.), which is insoluble in water. Currently, paclitaxel is administrated in physical admixture with a non-aqueous vehicle, cremophor-EL. This formulation, however, has several drawbacks. Hypersensitivity reactions have been associated with the vehicle and intravenous administration of the agent with this vehicle is also slow and causes discomfort to the patient.

Several methods have been suggested to enhance the aqueous solubility of paclitaxel. See, for example, PCT WO 93/24476, U.S. Pat. No. 5,362,831, and Nicolaou, et al. *Angew. Chem. Int. Ed. Engl.* (1994) 33, No. 15/16, pages 1583–1587. Preparing water-soluble prodrug versions has also been explored.

Prodrugs include chemical derivatives of a biologically-active parent compound which, upon administration, will eventually liberate the active parent compound in vivo. Use of prodrugs allows the artisan to modify the onset and/or duration of action in vivo. In addition, the use of prodrugs can modify the transportation, distribution or solubility of a drug in the body. Furthermore, prodrugs may reduce the toxicity and/or otherwise overcome difficulties encountered when administering pharmaceutical preparations.

A typical example in the preparation of prodrugs can involve conversion of alcohols or thioalcohols to either organic phosphates or esters. *Remington's Pharmaceutical Sciences,* 16th Ed., A. Osol, Ed. (1980), the disclosure of which is incorporated by reference herein.

Prodrugs are often biologically inert or substantially inactive forms of the parent or active compound. The rate of release of the active drug is influenced by several factors including the rate of hydrolysis of the converted ester or other functionality.

Recently, polyethylene glycol (PEG) and related polyalkylene oxides (PAO's) have been suggested as possible adjuncts for the preparation of paclitaxel prodrugs. See PCT WO 93/24476 supra, for example. PEG has also been conjugated to proteins, peptides and enzymes to increase aqueous solubility and circulating life in vivo as well as reduce antigenicity. See, for example, U.S. Pat. Nos. 5,298,643 and 5,321,095, both to Greenwald, et al. These latter two references disclose, inter alia, biologically-active conjugates having substantially hydrolysis-resistant bonds (linkages) between a polyalkylene oxide and the target moiety. Thus, long-lasting conjugates rather than prodrugs per se were prepared. In most situations, the average molecular weight of the polymer included in the conjugate was preferably about 5,000 daltons.

PCT WO 93/24476 discloses using an ester linkage to covalently bind paclitaxel to water-soluble polyethylene glycols and provide a prodrug. Applicants, however, have discovered that the ester linkages described therein provide $T_{1/2}$ for hydrolysis of greater than four days in aqueous environments. Thus, most of the conjugate is eliminated prior to hydrolysis being achieved in vivo. It would be preferable to provide an ester linkage which allows more rapid hydrolysis of the polymer-drug linkage in vivo so as to generate the parent drug compound more rapidly.

It has also been surprisingly found that when only one or two polymers of less than 10,000 molecular weight are conjugated to alkaloids and/or organic compounds, the resulting conjugates are rapidly eliminated in vivo. In fact, such conjugates are so rapidly cleared from the body that even if a hydrolysis-prone ester linkage is used, not enough of the parent molecule is regenerated in vivo to make the PAO-drug conjugate worthwhile as a prodrug.

Ohya, et al., J. *Bioactive and Compatible Polymers* Vol. 10 Jan., 1995, 51–66, disclose doxorubicin-PEG conjugates which are prepared by linking the two substituents via various linkages including esters. The molecular weight of the PEG used, however, is only about 5,000 at best. Thus, the true in vivo benefits would not be realized because the conjugates would be substantially excreted prior to sufficient hydrolysis of the linkage to generate the parent molecules.

Yamaoka, et al. *J. Pharmaceutical Sciences,* Vol. 83, No. 4, April 1994, pages 601–606, disclose that the half-life of unmodified PEG in circulation of mice after IV administration extended from 18 minutes to one day when molecular weight was increased from 6,000 to 190,000. Yamaoka, et al., however, failed to consider the effect of linking the polymer to a drug would have on the drug. Also, Yamaoka, et al. failed to consider that aqueous solutions of higher molecular weight polymers are quite viscous and difficult to dispense through the narrow-bore devices used to administer pharmaceutical preparations.

U.S. Pat. No. 4,943,579 discloses the use of certain amino acid esters in their salt forms as water soluble prodrugs. The reference does not, however, disclose using the amino acids as part of a linkage which would attach relatively high molecular weight polymers in order to form prodrugs. As evidenced by the data provided in Table 2 of the '579 patent, hydrolysis is quick. At physiologic pH, the insoluble base is rapidly generated after injection, binds to proteins and is quickly eliminated from the body before therapeutic effect can be achieved.

In summary, previous prodrugs based on conjugates of a parent drug compound and a water soluble polymer have not been successful for various reasons including excessively slow hydrolysis of the polymer from the parent drug and excessively rapid clearance of the prodrug from the body. In addition, improvements in prodrugs based on simple amino acid esters have been sought to overcome the rapid regeneration of the parent compound at physiological pH.

The present invention addresses the shortcomings described above.

SUMMARY OF THE INVENTION

In one aspect of the invention, compositions of formula (I) are provided:

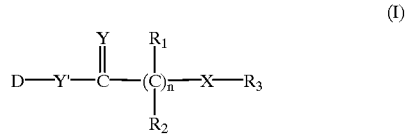
(I)

wherein:
D is a residue of biologically active moiety;
X is an electron withdrawing group;
Y and Y' are independently O or S;
(n) is zero (0) or a positive integer, preferably from 1 to about 12;
$R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;
$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

and $R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring.

In those aspects of the invention where $R_3$ is not a substantially non-antigenic polymer, the present invention includes pharmaceutically acceptable salts of the compounds of formula (I). In addition, when $R_3$ is

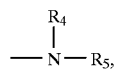

(n) is preferably 0 (zero) or an integer $\geq 2$.

In some preferred embodiments of the invention, $R_3$ includes both an alpha and an omega linking group so that two equivalents of a biologically active ingredient or drug, designated herein as D and/or D', can be delivered. Each D (or D') is attached to the polymer via a hydrolyzable ester linkage. Thus, polymer-based mono- and bis-prodrugs are contemplated.

The prodrugs preferably include a water-soluble polyalkylene oxide polymer as $R_3$. More preferably, $R_3$ is a polyethylene glycol and has a molecular weight of at least about 20,000.

In certain preferred aspects of the invention, the biologically active or parent compound (designated D or D' herein) attached to the polymer is a taxane such as paclitaxel or taxotere. In other aspects of the invention, the active or parent compound is camptothecin, etoposide, cis-platin derivatives containing OH groups, floxuridine or podophyllotoxin. In still further embodiments, other oncolytic agents, non-oncolytic agents such as anti-inflammatory agents, including steroidal compounds, as well as therapeutic low molecular weight peptides such as insulin are also contemplated.

For purposes of the present invention, it will be understood that the term "alkyl" shall be understood to include straight, branched or substituted $C_{1-12}$ alkyls, $C_{5-8}$ cycloalkyls or substituted cycloalkyls, etc.

One of the chief advantages of the compounds of the present invention is that the prodrugs achieve a proper balance between the rate of parent drug-polymer linkage hydrolysis and the rate of clearance of prodrug from the body. The linkage between the polymer and the parent compound, also referred to herein as a biologically-active nucleophile, hydrolyzes at a rate which allows a sufficient amount of the parent molecule to be released in vivo before clearance of the prodrug from the plasma or body.

Another advantage of the present invention is that in certain preferred embodiments, the prodrug composition includes a racemic mixture of the linker portion joining biologically active material linked to high molecular weight polymers using both the (d) and (l) forms of the prodrug linkage. This unique blend allows the artisan to design a novel prodrug complex having controlled release properties in which there is an initial relatively rapid release of the drug from the prodrug form, due to the relatively rapid enzymatic cleavage of the (l) forms of the amino acid linker portion, followed by a relatively slow release of the drug from the prodrug as a result of the hydrolysis of (d) form of the amino acid linker portion. Alternatively, the (d) and (l) forms of the amino acids can be used separately to employ the unique hydrolysis properties of each isomer, i.e. (l)- relatively rapid, (d)- slower hydrolysis. The compounds of the present invention are also designed to include polymers of adequate molecular weight to insure that the circulating life of the prodrugs is sufficient to allow the necessary amount of hydrolysis (and thus regeneration of therapeutic amounts of the drug in vivo) before elimination of the drug. Stated in another way, the compounds of the present invention are preferably designed so that the circulating life $T_{1/2}$, is greater than the hydrolysis $T_{1/2}$.

Methods of making and using the compositions described herein are also provided.

BRIEF DESCRIPTION OF THE DRAWINGS

FIG. 9 is a schematic representation of the reaction carried out in accordance with Example 30.

DETAILED DESCRIPTION OF THE INVENTION

A. THE PRODRUGS

Figure 1:
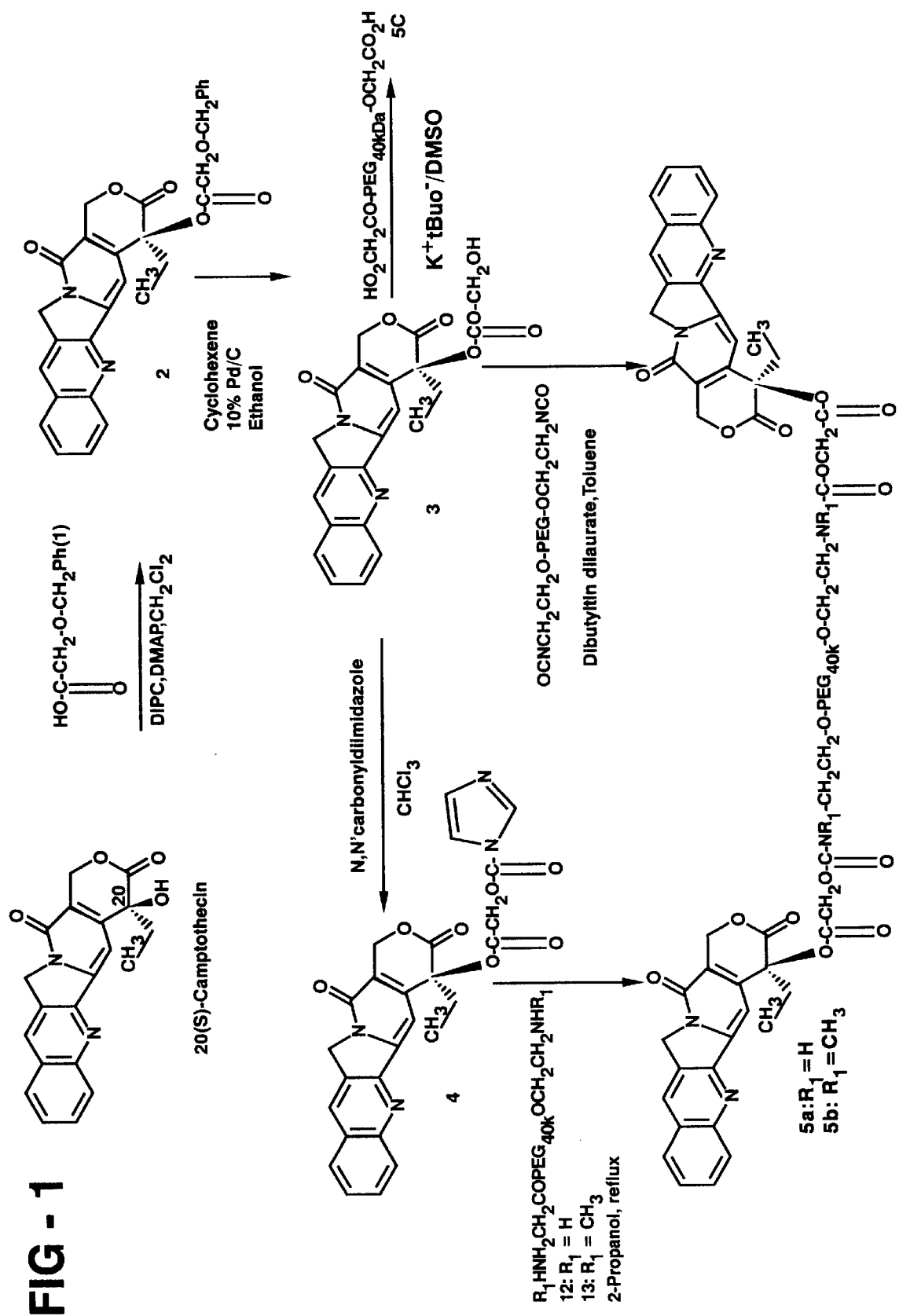
FIG. 1 is a schematic representation of the reactions carried out in accordance with Examples 1–5.

In most aspects of the invention, the prodrug compositions of the present invention contain hydrolyzable linkages between the polymer portion and a biologically active moiety derived from a biologically active moiety or nucleophile, i.e. native or unmodified drug. These linkages are preferably ester linkages designed to hydrolyze at a rate which generates sufficient amounts of the biologically active parent compound in a suitable time period so that therapeutic levels of the parent therapeutic moiety or moieties are delivered prior to excretion from or inactivation by the body. The term "sufficient amounts" for purposes of the present invention shall mean an amount which achieves a therapeutic effect as such effect is understood by those of ordinary skill in the art.

In one preferred embodiment of the invention, the prodrug compositions of the invention comprise the formula set forth below:

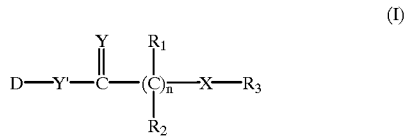
(I)

wherein:
D is a residue of a biologically active moiety;
X is an electron withdrawing group;
Y and Y' are independently O or S;
(n) is zero (0) or a positive integer, preferably from 1 to about 12;
$R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;
$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

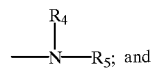
; and $R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring.

Preferably, the polymer portion, designated $R_3$ herein, is further substituted with a terminal capping moiety (Z) which is distal to the primary linkage attaching D to the polymer. A non-limiting list of suitable capping groups includes OH, $C_{1-4}$ alkyl moieties, biologically active and inactive moieties, or

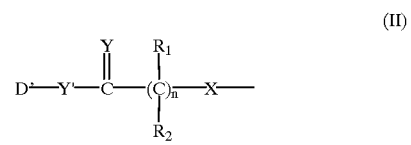
(II)

where D' is the same as D, a different biologically active moiety, a dialkyl urea, a $C_{1-4}$ alkyl, carboxylic acid or other capping group; and
Y, Y', $R_1$, $R_2$, X and (n) are as defined above.

Within Formula (I), Y and Y' are preferably oxygen and (n) is preferably 1.

In preferred aspects of the invention, the linkage attaching D to the polymer includes an amino acid ester spacer such as alanine. Thus, $R_1$ and $R_2$ are preferably one of H, methyl or ethyl. Alternatively, when one of $R_1$ and $R_2$ is H and the other is a substituted $C_{1-6}$ alkyl, it can be selected from carboxyalkyls, aminoalkyls, dialkylaminos, hydroxyalkyls, and mercaptoalkyls. In still further aspects of the invention, one of $R_1$ and $R_2$ is H and the other is an aryl such as phenyl or an aralkyl such as a benzyl or substituted benzyl.

In another embodiment, $R_1$ and $R_2$ are both not H when (n) is 1 (one) and $R_3$ is a polyalkylene oxide.

B. THE PRODRUG LINKAGE

1. The Electron Withdrawing Group X

Within the formula (I) described above, X is designated as an electron withdrawing group. In particular, X can be selected from moieties such as O, $NR_1$, S, SO and $SO_2$ where $R_1$ is as defined above. Preferably, however, when included as part of X, $R_1$ is H, a $C_{1-6}$ alkyl or substituted $C_{1-6}$ alky. For purposes of the present invention when (n) is 1 in Formulas (I) and (II), X is preferably a moiety which gives a substituted acetic acid with a pKa of less than about 4.0 upon hydrolysis of the prodrug ester. The moieties selected for X within the formula promote relatively rapid hydrolysis because of the low pKa of the resulting substituted acetic acid.

On the other hand, when (n) is zero (0) and X is oxygen and Y and Y' are oxygen or sulfur, a carbonate or thiocarbonate linkage is formed. The carbonate linkage may also be cleaved by enzymes such as esterases located in the plasma, as well as near or within the tumor area given the enhanced permeation and retention effect which occurs in solid tumors. See Greenwald, R. B. *Exp. Opin. Ther. Patents* (1997) 7(6):601–609. Representative examples of carbonate derivatives are described in Examples 47, 48, 49, 51a, 51b, 52, and 53.

Similarly, when (n) is zero (0), X is $NR_1$ and Y and Y' are oxygen or sulfur, a carbamate or thiocarbamate is formed. This linkage is more stable than carbonate or ester linkages but nonetheless may also be cleaved by a variety of enzymes such as proteases and peptidases, largely in the tumor region. The drug is then targeted in the same manner as carbamate or thiocarbamate linkages described above. Representative examples are described in Examples 50a and 50b.

2. The Amino Acid Portion of the Linker

Figure 6:
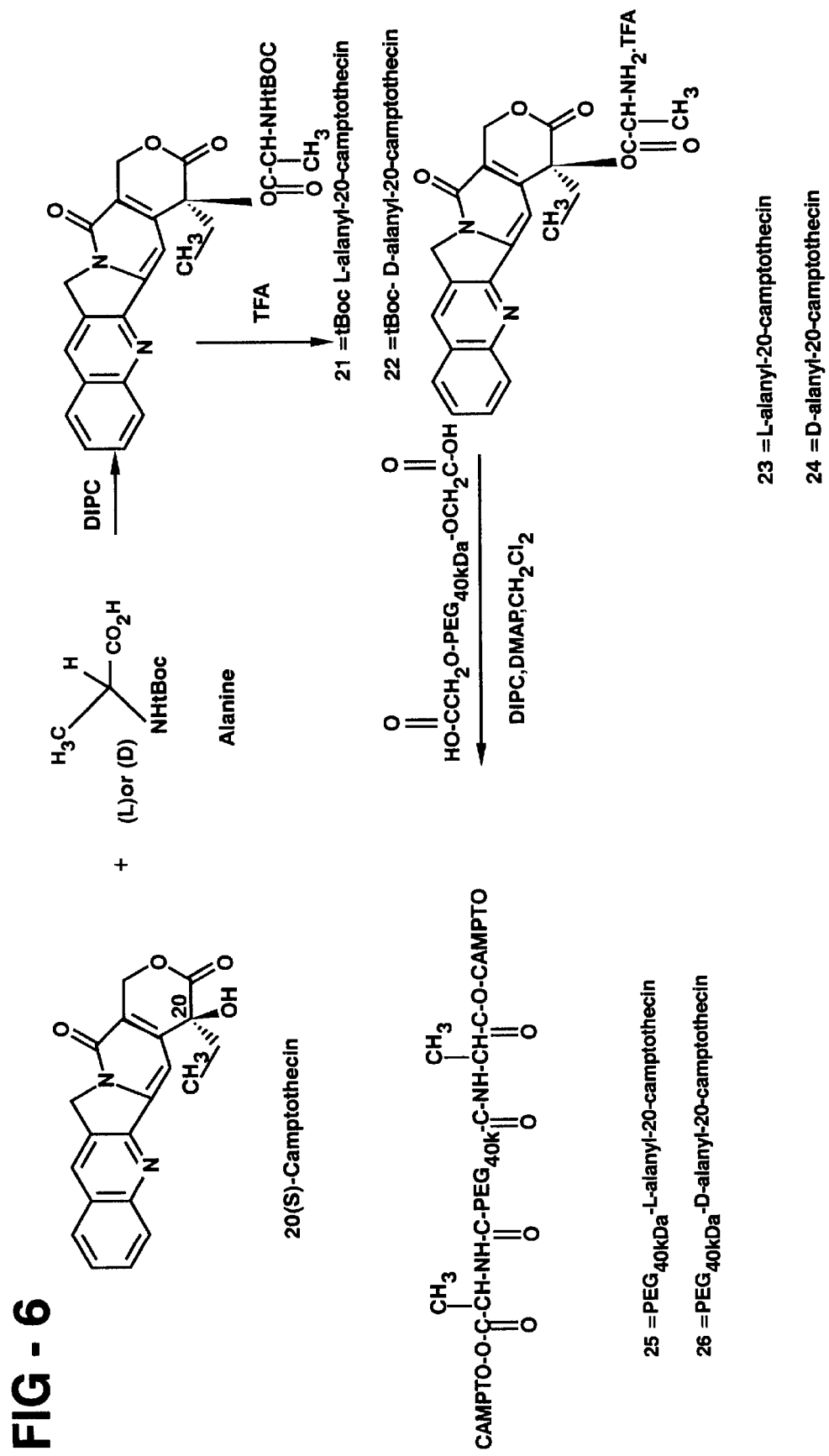
FIGS. 6 and 7 are schematic representations of the reactions carried out in accordance with Examples 21–28.

As mentioned above in Section A, one aspect of the invention includes using an amino acid ester spacer such as alanine within the linkage attaching the polymer $R_2$ to the biologically active moiety D. This portion of the linkage can be attached to the D portion directly as illustrated in FIG. 6 using t-Boc-l (or d or racemic)-alanine or by converting a PEG acid or diacid with the l- or d-alanine-t-butyl ester as shown, for example, in FIG. 7.

3. Hydrolysis and Parent Drug Regeneration

The prodrug compounds of the present invention are designed so that in plasma the $T_{1/2}$, circulation is greater than the $T_{1/2}$ hydrolysis, which in turn is greater than the $T_{1/2}$ for elimination, i.e.

$T_{1/2}$ circulation > $T_{1/2}$ hydrolysis > $T_{1/2}$ elimination.

The prior art had several shortcomings associated with its approach to providing polymer based prodrugs. For example, in some cases, the molecular weight of the polymer was insufficient, i.e. 10,000 Daltons or less, regardless of the linkage used to attach the parent drug to the polymer. In other cases, a polymer of sufficient molecular weight was proposed but the linkage was not designed to allow sufficient in vivo hydrolysis and release of the parent molecule. The compounds of the present invention overcome these shortcomings by including not only polymers of sufficient weight but also linkages which meet the criteria discussed above.

Regardless of whether (n) is 1, as preferred in the embodiment discussed above in B1, the ester-based linkages included in the compounds have a $T_{1/2}$ hydrolysis in the plasma of the mammal being treated which is long enough to allow the parent compounds to be released prior to elimination. Some preferred compounds of the present invention have plasma $T_{1/2}$ hydrolysis rates ranging from about 30 minutes to about 12 hours. Preferably, the compositions have a plasma $T_{1/2}$ hydrolysis ranging from about 1 to about 8 hours and most preferably from about 2.5 to about 5.5 hours. The compounds thus provide a distinct advantage over the rapidly hydrolyzed prodrugs of the prior art, such as those described in U.S. Pat. No. 4,943,579 which are all about 45 minutes or less and are of limited practical value. The parent compounds appear to be rapidly regenerated in vivo and quickly eliminated from circulation. While Applicants are not bound by theory, in those aspects of the invention where prodrugs are formed, regeneration of sufficient amounts of the parent compound during the time the prodrug remains in circulation is believed to be a key to providing an effective prodrug compositions.

C. SUBSTANTIALLY NON-ANTIGENIC POLYMERS

The prodrug compositions of the present invention include a water-soluble polymer, $R_3$. Suitable examples of such polymers include polyalkylene oxides such as polyethylene glycols which are also preferably substantially non-antigenic. The general formula for PEG and its derivatives, i.e. R"—$(CH_2CH_2O)_x$—$(CH_2)_y$—R', where (x) represents the degree of polymerization or number of repeating units in the polymer chain and is dependent on the molecular weight of the polymer, (y) represents a positive integer, R' is $(CHR_1)$ and R" is a capping group as defined herein or R'. It will be understood that the water-soluble polymer will be functionalized for attachment to the linkage designated X herein. As an example, the PEG can be functionalized in the following non-limiting manner:

—C(Y)—$(CH_2)_n$—$(CH_2CH_2O)_x$—R",
—C(Y)—Y—$(CH_2)_n$—$(CH_2CH_2O)_x$—R",
—C(Y)—$NR_1$—$(CH_2)_n$—$(CH_2CH_2O)_x$—R",
—$CR_1R_2$—$(CH_2)_n$—$(CH_2CH_2O)_x$—R".

where Y, R", $R_1$, $R_2$, (n) and (x) are as defined above.

In particular, polyethylene glycols (PEG's), monoactivated, $C_{1-4}$ alkyl-terminated PAO's such as monomethyl-terminated polyethylene glycols (mPEG's) are preferred when mono- substituted polymers are desired; bis-activated polyethylene oxides are preferred when disubstituted prodrugs are desired. In order to provide the desired hydrolyzable linkage, mono- or di-acid activated polymers such as PEG acids or PEG diacids are used. Suitable PAO acids can be synthesized by converting mPEG-OH to an ethyl ester. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester. See, for example, commonly assigned U.S. patent application Ser. No. 08/440,732 filed May 15, 1995. The disclosures of each of the foregoing are incorporated by reference herein.

Although PAO's and PEG's can vary substantially in molecular weight, polymers having molecular weight ranges of at least 20,000 are preferred. Polymers ranging from about 20,000 to about 80,000 are usually selected for the purposes of the present invention. Molecular weights of from about 25,000 to about 45,000 are preferred and 30,000 to about 42,000 are particularly preferred. The molecular weight of the polymer selected for inclusion in the prodrug must be sufficient so as to provide sufficient circulation of the prodrug during hydrolysis of the linker.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, HPMA's and the like can be used if the same type of ester activation is employed as described herein for PAO's such as PEG, i.e. conversion of alcohol to a 2-alkoxy acid. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

As mentioned above, the prodrugs of the present invention include one or two equivalents of drug per equivalent of $R_3$, i.e. the polymer. As such, preferred polymers can be functionalized to form the bis-prodrugs when reacted with a sufficient amount of a parent compound. One preferred polymer-linkage combination is represented below as formula (III):

(III)

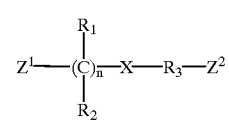

wherein:

$R_{1-3}$, X and n are the same as that set forth above for (I);

$Z^1$ and $Z^2$ are independently $CO_2H$, $CO_2R_6$, $OR_7$, $CONR_1R_8$, H, a $C_{1-4}$ alkyl or

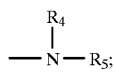

where $R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring;

$R_6$ is $R_4$ or an N-hydroxysuccinimide, an N-hydroxybenzotriazole, an N-acyl thazolidine, imidazole or an acid activating group;

$R_7$ is $R_4$ or C(O)-halogen, para nitrophenyl carbonate, imidazolyl carbonate, or N-hydroxysuccinirnidyl carbonate; and $R_8$ is $R_4$ or $CR_1R_2CO_2H$.

In certain aspects of the invention, $R_3$ has a molecular weight of about 20,000 or greater. Although, the prodrugs of the present invention can be formed using any of the substantially non-antigenic polymers described herein, the following polyalkylene oxide derivatives, i.e. PEG diamines, PEG-acids and PEG-diacids are especially preferred for use in formation of the prodrug:

a) $R_4\ NR_5$—$(CH_2)_n$—O—PEG—O—$(CH_2)_n$—$NR_4R_5$, b) $HO_2C(CH_2)_nS$—$(CH_2)_2$—O—PEG—O—$(CH_2)_2$—S—$(CH_2)_nCO_2H$;

c) $HO_2C$—$CH_2$—O—PEG—O—$CH_2$—$CO_2H$;

d)
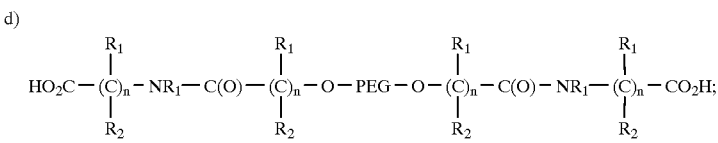

e)
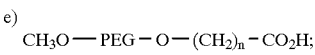

where $R_1$, $R_2$, and (n) are the same as defined above for Formula (I).

It will be clear from the foregoing that other polyalkylene oxide derivatives of the foregoing, such as the polypropylene glycol acids, POG acids, etc., as well as other bifunctional linking groups are also contemplated.

D. PRODRUG CANDIDATE

1. Taxanes and Taxane Derivatives

One class of compounds included in the prodrug compositions of the present invention is taxanes. For purposes of the present invention, the term "taxane" includes all compounds within the taxane family of terpenes. Thus, taxol (paclitaxel), 3'-substituted t-butoxy-carbonyl-amine derivatives (taxoteres) and the like as well as other analogs available from, for example, Sigma Chemical of St. Louis, Mo. are within the scope of the present invention. Representative taxanes are shown below.

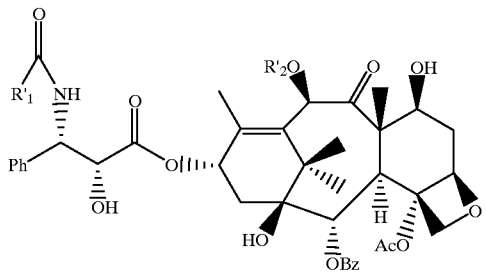

Paclitaxel: $R_1' = C_6H_5$; $R_2' = CH_3CO$

Taxotere: $R_1' = (CH_3)_3CO$; $R_2' = H$

These compounds have been found to be effective anti-cancer agents. Numerous studies indicate that the agents have activity against several malignancies. To date, their use has been severely limited by, among other things, their short supply, poor water solubility and hypersensitivity. It is to be understood that other taxanes including the 7-aryl-carbamates and 7-carbazates disclosed in commonly assigned U.S. Pat. Nos. 5,622,986 and 5,547,981 can also be included in the prodrugs of the present invention. The contents of the foregoing U.S. patents are incorporated herein by reference.

Although the examples describe inter alia paclitaxel for illustrative purposes, it is to be understood that the methods described herein are suitable for all taxanes and related molecules. The only limitation on this provision is that the selected taxanes must be capable of undergoing 2' position modifications described herein. Paclitaxel, however, is a preferred taxane.

Synthesis of the taxane-based prodrugs of the invention is set forth below in section E and in the Examples. In general, however, a taxane having the 2'-position available for substitution is reacted with a suitably activated polymer such as a PEG acid under conditions sufficient to cause the formation of a 2' ester linkage between the two substituents. The corresponding diester can be prepared by reacting at least about 2 equivalents of taxane per polymer diacid. Even when two equivalents of taxane are reacted with the polymer diacid, the resulting conjugate can contain minor amounts (i.e. up to 25%) by weight of a monoester species containing an acyl urea or carboxylic acid distal to the polymer-taxane linkage with regard to the polymer. These compositions are also capable of delivering a biological effect. It is preferred that the polymer acid have a molecular weight of at least about 20,000. See FIGS. 5 and 8 as illustrative examples.

2. Camptothecin and Related Topoisomerase I Inhibitors

Camptothecin is a water-insoluble cytotoxic alkaloid produced by *camptoteca accuminata* trees indigenous to China and *nothapodtes foetida* trees indigenous to India. Camptothecin and related compounds and analogs are also known to be potential anticancer or antitumor agents and have been shown to exhibit these activities in vitro and in vivo. Camptothecin and related compounds are also candidates for conversion to the prodrugs of the present invention. See, for example, U.S. Pat. No. 5,004,758 and Hawkins, *Oncology*, December 1992, pages 17–23. Camptothecin and related analogues have the structure:

TABLE 1

| NETWORK TYPE | AGGREGATE PHYSICAL LAYER BANDWIDTH | |
|---|---|---|
| FDDI | 100 | Mbps |
| Fast Ethernet | 100 | Mbps |
| 100 VG-AnyLAN | 100 | Mbps |
| 25 Mbps ATM | 50 | Mbps |
| OC3c ATM | 310 | Mbps |
| OC-12c ATM | 1.244 | Gbps |

Additional comptothecin analogs include those reported in the literature including the 10-hydroxycamptothecins, 11-hydroxycamptothecins and/or 10,11-dihydroxycamptothecins, 7-and/or 9-alkyl, substituted alkyl, cycloalkyl, alkoxy, alkenyl, aminoalkyl, etc. camptothecins, A-ring substituted camptothecins such as 10,11-alkylenedioxycamptothecins, such as those disclosed in U.S. Pat. No. 5,646,159, the contents of which are incorporated herein by reference, etc.

Formation of a monoester camptothecin prodrug can be accomplished by reacting one or more equivalents of a suitably (acid) activated polymer with one equivalent of the camptothecin derivative under conditions sufficient to effectively convert the 20- OH to an ester-linked polymeric based prodrug. Camptothecin diesters are similarly prepared by reacting at least about 2 and preferably greater equivalents of the camptothecin with a suitably prepared PAO diacid. Details concerning the reaction schemes and conditions are provided in Section E, below, FIGS. 1, 2, 4, etc. and in the Examples.

In addition to the foregoing camptothecin analogs, it has been found that new 20(S)camptothecin-mono-PEG ester compounds can be formed when a diacid PEG is used with certain carbodiimide condensing agents with the appropriate stoichiometry. For example, the alpha terminus of the polymer is converted to a camptothecin-PEG ester and the omega terminus of the PEG diacid is converted from the acid to an acyl dialkyl urea, depending on the dialkyl carbodiimide employed to effect conjugation. These derivatives show antitumor activity in vivo and upon NMR inspection, cross-linking was found to be negligible. In most preferred aspects, however, bis- prodrug camptothecin compositions are formed by linking each of the alpha and omega termini of the polymer via Y' to the 20S position of camptothecin when a carbodiimide is used as the condensing agent. In alternative aspects, higher amounts of the diester can be obtained by the use of a Mukaiyama reagent, i.e. 2-chloro-1-methylpyridinium iodide.

3. Additional Biologically-Active Moieties

In addition to the foregoing molecules, the prodrug formulations of the present invention can be prepared using many other compounds. For example, biologically-active compounds such as cis-platin derivatives containing OH groups, i.e.

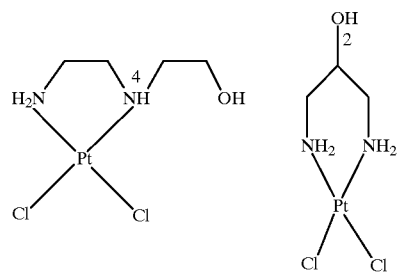

mono- and bis-PEG esters derived from floxuridine, shown below:

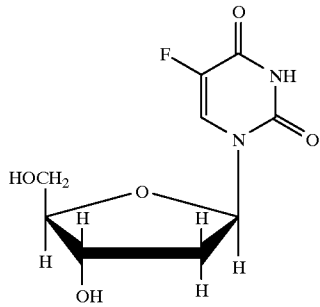

podophyllotoxin, shown below:

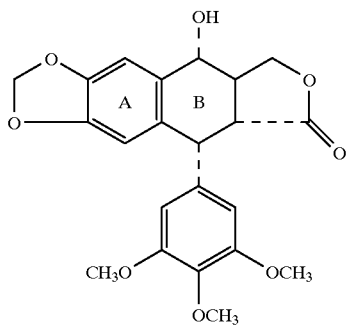

and related compounds can be included. The prodrug ester can be formed at the 2-hydroxy position for the "A" cis-platin derivative, the 2-hydroxyethyl position of the "B" cis-platin derivative, the 3' and 5' hydroxy positions of floxuridine and at the C-4 hydroxy for podophyllotoxin. These prodrug compositions can be prepared, for example, using the technique described for preparing compound 32 in Example 31.

The parent compounds selected for prodrug forms need not be substantially water-insoluble, although the polymer-based prodrugs of the present invention are especially well suited for delivering such water-insoluble compounds. Other useful parent compounds include, for example, certain low molecular weight biologically active proteins, enzymes and peptides, including peptido glycans, as well as other anti-tumor agents, cardiovascular agents such as forskolin, anti-neoplastics such as combretastatin, vinblastine, vincristine, doxorubicin, AraC, maytansine, etc. anti-infectives such as vancomycin, erythromycin, etc. anti-fungals such as nystatin or amphoteracin B, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

The foregoing is illustrative of the biologically active moieties which are suitable for the prodrugs of the present invention. It is to be understood that those biologically active materials not specifically mentioned but having suitable ester-forming groups, i.e. hydroxyl moieties, are also intended and are within the scope of the present invention. It is also to be understood that the prodrug conjugates of the present invention may also include compounds containing not only one equivalent of drug and polymer but also a moiety which does not effect bioactivity in vivo. For example, it has been found that in some instances, in spite of reacting diacids with drug molecules having a single linkage point, the reaction conditions do not provide prodrugs with two equivalents of drug per polymer. On the contrary, the prodrugs contain only one equivalent of drug per polymer. By-products of the reactants such as acyl ureas can be formed. Furthermore, it has also been found that in spite of the reaction with a bis-activated polymer, the prodrugs are remarkably free of cross-linked species.

The only limitation on the types of molecules suitable for inclusion herein is that there is at least one position on which the hydrolyzable linkage can be attached, so that after prodrug administration, the prodrug can regenerate sufficient quantities of the parent compound in vivo.

E. SYNTHESIS OF PRODRUGS

Generally, the prodrugs of the invention are prepared by:
1) providing an activated polymer, such as a PEG-acid or PEG-diacid and a parent compound having a position thereon which will allow a hydrolyzable linkage to form, and
2) reacting the two substituents in an inert solvent such as methylene chloride, chloroform, toluene or BMF in the presence of a coupling reagent such as 1,3-diisopropylcarbodiimide (DIPC), 1,(3-dimethyl aminopropyl) 3-ethyl carbodiimide (EDC), any suitable dialkyl carbodimide, Mukaiyama reagents, (e.g. 2-halo-1-alkyl-pyridinium halides) or propane phosphonic acid cyclic anhydride (PPACA), etc. which are available, for example from commercial sources such as Sigma Chemical, or synthesized using known techniques and a base such as dimethylaminopyridine (preferred), diisopropyl ethylamine, pyridine, triethylamine, etc. at a temperature from 0° C. up to 22° C. (room temperature).

In another preferred aspect of this embodiment, the synthesis method provides polymer-based prodrugs having a circulation half-life greater than their in-vivo hydrolysis half-life. The method includes:
reacting a biologically active moiety containing an available hydroxyl group with a bifunctional spacer moiety containing an available carboxylic acid group in the presence of a first coupling agent to form a biologically active moiety—spacer prodrug intermediate,
reacting the biologically active moiety—spacer prodrug intermediate with a substantially non-antigenic polymer containing a terminal carboxylic acid group or a terminal amine or hydroxy group in the presence of a second coupling agent and recovering the polymer-based prodrug.

The first and second coupling agents can be the same or different.

Examples of suitable bifunctional spacer groups include diglycolic acid, thiodiglycolic acid, l-alanine and d-alanine, hydroxyacetic acid, bromoacetic acid, etc.

An illustrative example of method of preparing the conjugates using camptothecin derivatives as the prototypical biologically active nucleophile includes the steps of:
forming a camptothecin derivative containing bifunctional spacer containing moiety, by contacting the camptothecin derivative with a bifunctional spacer containing moiety such as tBoc, d or l alanine in the presence of a coupling agent such as DIPC or PPAC;
forming the trihaloacetic acid deriviative of the camptothecin derivative containing the bifunctional spacer containing moiety such as the trifluoroacetic acid salt; and
reacting the trihaloacetic acid derivative of the camptothecin derivative containing the bifunctional spacer containing moiety with a diacid derivative of a substantially non-antigenic polymer such as a PEG diacid. The resultant compound is recovered using known techniques.

Alternative and specific syntheses are provided in the examples. One particular alternative, however, includes derivatizing the biologically active moiety in the position desired for the linkage and thereafter reacting the derivative with an activated polymer.

F. NON-POLYMERIC DERIVATIVES

In certain other aspects of the invention, the compounds of formula (I) are non-polymeric derivatives, i.e. $R_3$ is other than a substantially non-antigenic polymer. $R_3$, instead is a $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

$R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring. It is preferred that when $R_3$

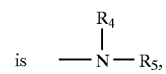

(n) is preferably 0 (zero) or an integer $\geq 2$.

The compounds of this aspect of the invention are thus simple carbonate, simple carbamate derivatives and the like and can have utility either therapeutically as is or as pharmaceutically acceptable salts such as the sodium salt. Preparation of such salts will be apparent to those of ordinary skill without undue experimentation. These compounds are also useful as intermediates which can be further processed into prodrugs. For example, when $R_3$ is a substituted alkyl or cycloalkyl, substituted aryl or heteroaryl, or substituted aralkyl, these intermediate compounds can be reacted with activated polymers as described herein to form prodrugs. In particular, if $R_3$ is an aminoalkyl such as aminopropyl, aminobutyl, aminoethyl, etc., the intermediate can be reacted with non-antigenic polymer containing a succinimidyl carbonate activated, cyclic imide thione activated polymer or with an acid derivative of the polymer using a condensing agent. Similarly, if $R_3$ is a carboxyalkyl such as a carboxypropyl, carboxybutyl, carboxyethyl, etc., the intermediate is reacted with an amine-activated substantially non-antigenic polymer such as a PEG-amine. Alternatively, if R$_3$ is a hydroxyalkyl such as a hydroxypropyl, hydroxybutyl, hydroxyethyl, etc., the intermediate is reacted with an isocyanate or isothiocyante activated substantially non-antigenic polymer such as a PEG-NCO or PEG-NCS. Simple amino acid esters of the non-polymeric derivatives of the present invention are also contemplated.

G. METHODS OF TREATMENT

Another aspect of the present invention provides methods of treatment for various medical conditions in mammals. The methods include administering to the mammal in need of such treatment, an effective amount of a prodrug, such as a paclitaxel 2'-PEG ester, which has been prepared as described herein. The compositions are useful for, among other things, treating neoplastic disease, reducing tumor burden, preventing metastasis of neoplasms and preventing recurrences of tumor/neoplastic growths in mammals.

The amount of the prodrug administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug taxanes are administered in amounts ranging from about 5 to about 500 mg/m$^2$ per day, based on the amount of the taxane moiety. Camptothecin and podophyllotoxin prodrugs are also administered in amounts ranging from about 5 to about 500 mg/m$^2$ per day. The range set forth above is illustrative and those skilled in the art will determine the optimal dosing of the prodrug selected based on clinical experience and the treatment indication.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. In preferred aspects of the invention, however, the prodrugs are parenterally administered to mammals in need thereof.

H. EXAMPLES

The following examples serve to provide further appreciation of the invention but are not meant in any way to restrict the effective scope of the invention. The numbers shown in bold in parentheses in the Examples correspond to the compounds shown in the schematic diagrams set forth in the Figures.

EXAMPLE 1

Camptothecin-20-O-ester of benzyloxyacetic acid—Compound 2

Referring now to FIG. 1, benzyloxyacetic acid 1 (2 g, 12.06 mmol), prepared by the aqueous hydrolysis of benzyloxyacetyl chloride, (Aldrich) diisopropylcarbodiimide (DIPC, 1.9 ml, 12.06 mmol) and dimethylaminopyridine (DMAP, 982 mg, 8.04 mmol) were added to a suspension of camptothecin, (1.4 g, 4.02 mmol) in CH$_2$Cl$_2$ (500 ml) at 0° C. Stirring was continued for 3 hours. The resulting yellow solution was concentrated to about 100 ml and washed with 1N hydrochloric acid (10 ml×2), followed by 1% aqueous sodium bicarbonate solution (10 ml×2). The organic layer was dried (anhydrous MgSO$_4$) and evaporated in vacuo to give a yellow solid which was recrystallized from ethyl acetate. The product was then triturated with methanol (10 ml), and the slurry filtered to yield 2 (1.3 g, 65%).

$^1$HNMR(CDCl$_3$)δ:1.0(t), 1.84(s), 2.1–2.3(m), 4.31(s), 4.59–4.69(q), 5.28(s), 5.4–5.8(dd), 7.22(s), 7.27(s), 7.3–7.38 (m), 7.6–7.7(m), 7.81–7.87(m), 7.92–7.95(d), 8.19–8.22(d), 8.39(s). $^{13}$CNMR(CDCl$_3$)δ: 7.52, 31.74, 49.90, 66.59, 67.16, 73.27, 76.38, 95.80, 120.27, 127.97, 128.10, 128.43, 129.54, 130.63, 131.15, 136.81, 145.39, 146.36, 148.81, 152.22, 157.26, 167.19, 169.52.

EXAMPLE 2

Camptothecin-20-O-ester of hydroxyacetic acid—Compound 3

Continuing with reference to FIG. 1, a suspension of 2 (1 g, 2.01 mmol) and 10% Pd/C (500 mg) in ethanol (100 mL) was degassed by sparging with nitrogen, followed by the addition of cyclohexene (5 mL). The reaction mixture was heated at reflux for 20 hours and the catalyst was filtered. Removal of solvent in vacuo followed by recrystallization from acetonitrile gave 3 (500 mg, 50%).

$^1$HNMR (DMSO-D6)δ: 1.0(t), 1.84(s), 2.1–2.3(m), 3.1 (s), 4.31(s), 4.0–4.69(m), 5.28(s), 5.6(m), 5.8(m), 7.22(s), 7.6–7.7(m), 7.6–7.95(m), 8.0–8.2(m), 8.3(s), 8.7(s). $^{13}$C NMR (DMSO-D6)δ7.5, 30.14, 50.20, 59.37, 66.21, 75.83, 79.14, 94.95, 118.84, 127.71, 127.97, 128.52, 128.87, 129.77, 130.42, 131.58, 145.35, 145.95, 147.85, 152.29, 156.53, 167.21, 171.69.

EXAMPLE 3

Camptothecin-20-O-ester of 2-imidazolyl carbonyloxyacetic acid—Compound 4:

As schematically shown in FIG. 1, a solution of 3 (240 mg, 0.59 mmol), N,N-carbonyldiimidazole (288 mg, 1.77 mmol) in chloroform (80 mL) was stirred at 50° C. for 18 hours. Removal of solvent in vacuo followed by trituration with ethyl acetate gave 4 as a pale yellow solid (170 mg, 58%).

$^1$H NMR (CDCl$_3$)δ:1.0(t), 2.1–2.5(m), 5.1(d), 5.28(s), 5.4–5.8(dd), 7.0(s), 7.5(s), 7.7(m), 7.9(m), 8(d), 8.1(s), 8.3 (d), 8.4(s).

EXAMPLE 4

Camptothecin-20-O-ester of 2-PEG$_{40kDa}$carbamoylacetic acid—Compound 5a

Method A

As shown in FIG. 1, a solution of 3 (60.4 mg, 0.148 mmol), PEG$_{40k}$diisocyanate (2 g, 0.05 mmol), dibutyl tin dilaurate (15.7 mg, 0.024 mmol) in dichloromethane (20 mL) was refluxed for 18 hours. Removal of the solvent in vacuo and recrystallization from 2-propanol (10 mL) gave 5a.

EXAMPLE 5

Camptothecin-20-O-ester of 2-PEG$_{40kDa}$carbamoylacetic acid—Compound 5a

Method B

As illustrated in FIG. 1, solution of 4 (74 mg, 0.148 mmol) and PEG$_{40kDa}$ diamine (12, g, 0.05 mmol) in 2-propanol (20 ml) was refluxed for 12 hours. The solvent was removed under reduced pressure to yield 5a as a solid which was recrystallized from 2-propanol (1.6 g, 79%).

EXAMPLE 6 a) Camptothecin-20-O-ester of 2-PEG$_{40k}$N-methylcarbamoyl acetic acid—Compound 5b FIG. 1 also shows formation of compound 5b. Compound 5b was prepared in a similar manner as that used to prepare compound 5a in Example 5 (method B), using PEG$_{40k}$N-methyldiamine 13 as a starting material.

$^{13}$CNMR(CDCl$_3$)δ: 166.63, 166.08, 156.17, 151.39, 147.84, 145.41, 144.35, 130.84, 130.03, 128.95, 127.99, 127.71, 127.61, 127.40, 118.68, 94.30, 76.72, 65.66–71.65 (PEG), 61.3, 49.37, 48.52, 48.15, 47.82, 35.14, 34.54, 33.15, 30.97, 21.62, 6.97.

b) PEG$_{40k}$ dicarboxylic acid ester of 20-O-hydroxyacetyl Camptothecin—Compound 5c FIG. 1 also illustrates formation of compound 5c. PEG 40$_{kDa}$dicarboxylic acid (3 grams, 0.075 mmol) was azeotroped in toluene (100 ml) for 1 hour. Potassium t-butoxide, 1.0M solution (165 μl, 0.165 mmol) was added to the solution and the contents were refluxed for 2 hours. The solvent was removed under reduced pressure and the solid obtained was redissolved in DMSO (30 ml). Compound 3 (140 mg, 0.299 mmol) was added to this solution and the reaction mixture was stirred at room temperature for 18 hours. Ether (100 ml) was added and the solid precipitated was collected by filtration and recrystallized from 2-propanol to yield 5c.

EXAMPLE 7

Mono t-butyl ester of diglycolic acid 6

Figure 2:
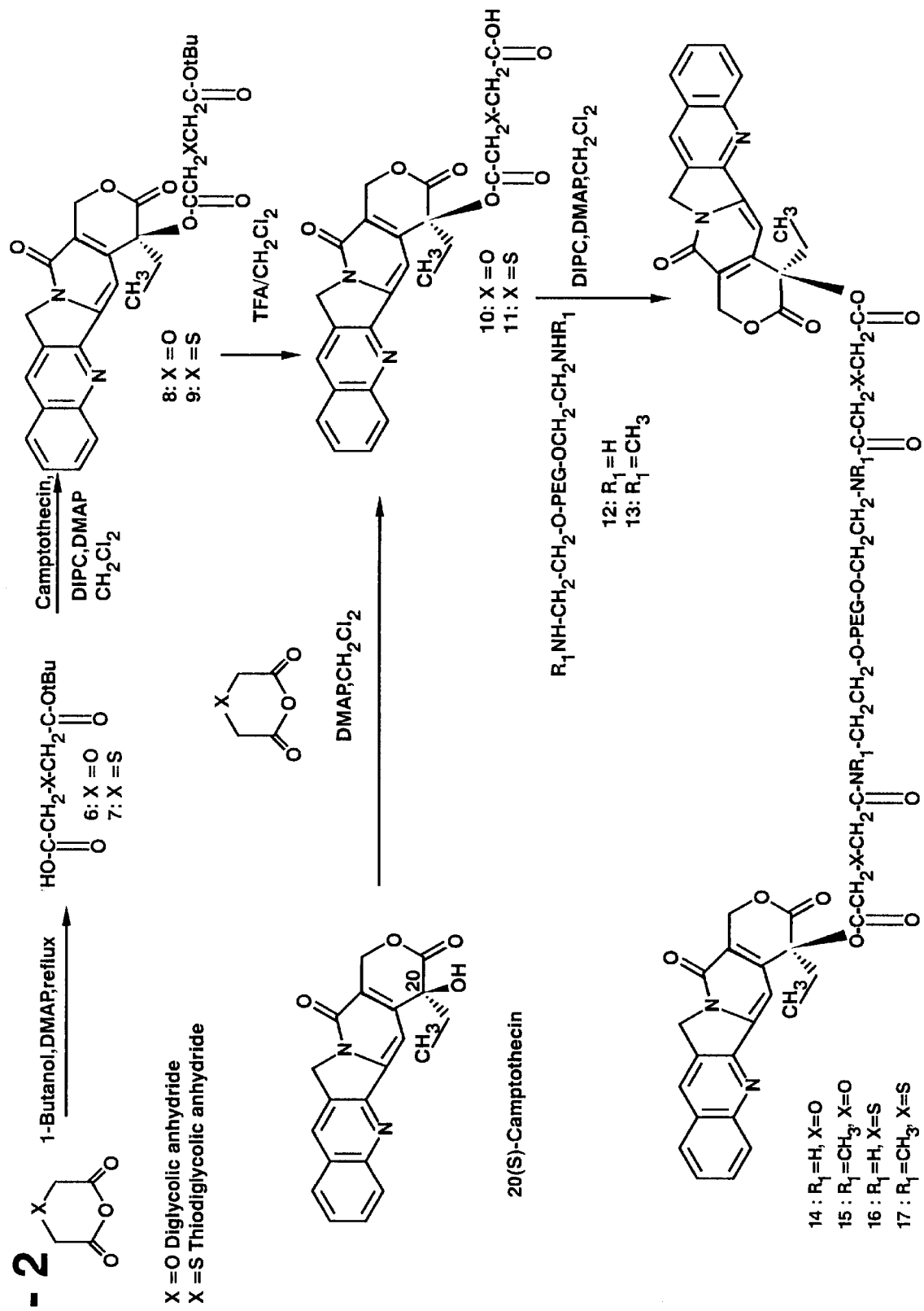
FIG. 2 is a schematic representation of the reactions carried out in accordance with Examples 6–17.

Referring now to FIG. 2, a solution of diglycolic anhydride (10 g, 0.09 mol) and DMAP (10.5 g, 0.09 mol) in dry t-butanol (75 ml) was stirred at reflux temperature for 18 hours. The solvent was removed under reduced pressure and the residue was dissolved in water (100 ml). The aqueous solution was acidified to pH 2.5 to 3.0 with 1N HCl and extracted with dichloromethane. Removal of solvent from the dried extracts yielded 12.3 g (75%) of the mono t-butyl ester of glycolic acid 6. $^{13}$C NMR (CDCl$_3$)δ:172.85, 169.54, 82.42, 68, 78, 68.45, 27.84.

EXAMPLE 8

Camptothecin-20-O-ester of 6—Compound 8

Continuing with reference to FIG. 2, a mixture of 6, (4.2 g, 0.02 mol), camptothecin (4.0 g, 0.01 mol), dimethylamino pyridine (DMAP, 2.7 g, 0.02 mol), and diisopropylcarbodiimide (DIPC 2.8 g, 0.02 mol) in anhydrous dichloromethane (40 ml) was stirred for 18 hours at room temperature. The reaction mixture was washed with water, then saturated aqueous sodium bicarbonate, 0.1N HCl and again with water. The organic layer was dried (anhyd.MgSO$_4$) and the solvent removed in vacuo. Recrystallization of the resultant solid from dichloromethane/ether gave 8, (3.1 g, 54%).

$^1$HNMR (CDCl$_3$)δ: 8.35(s), 8.15–8.18(d), 7.89–7.92(d), 7.80(m), 7.63–7.66(m), 7.20(s), 5.35–5.72 (ABq), 5.21(s), 4.45–4.48(d), 4.11–4.13(d), 2.2–2.3(m), 1.45(s), 1.00(t).

$^{13}$CNMR(CDCl$_3$)δ: 168.97, 168.52, 166.98, 157, 151.94, 148.55, 146.25, 145.13, 130.97, 130.39, 129.32, 128.21, 127.99, 127.76, 119.94, 95.54, 81.75, 76.38, 68.36, 67.45, 66.96, 49.72, 31.53, 27.86, 7.38.

EXAMPLE 9

Camptothecin-20-O-ester of diglycolic acid 10

Continuing with reference to FIG. 2, compound 8 (0.8 g, 1.5 mmol) in dichloromethane-trifluroacetic acid solution (12 ml, 8:4) was stirred at room temperature for 30 minutes. The solvent was removed under reduced pressure, and the resulting solid was recrystallized from dichloromethane/ether to yield 10 (0.6 g, 82%).

The final product 10 can also be made directly by condensing 20(S) camptothecin with diglycolic anhydride in methylene chloride and the presence of DMAP.

$^1$H NMR (CDCl$_3$)δ: 8.44(s), 8.27–8.34(m), 7.95(d), 7.86 (m)7.70(m), 7.34(s), 5.37–5.75(ABq,) 5.31(s), 4.47–4.5(d), 4.39–4.41(d)2.18–2.26(m), 1.03(t).$^{13}$C NMR (DMSO-D$_6$)δ: 171.15, 169.27, 167.41, 156.84, 152.63, 148.19, 146.41, 145.45, 131.88, 130.71, 130.11, 129.22, 128.83, 128.29, 128.02, 119.08, 95.24, 76.72, 67.57, 67.33, 66.62, 50.54, 30.47, 7.84.

EXAMPLE 10

PEG$_{40kDa}$di-N-methylamine hydrochloride 12

Continuing with reference to FIG. 2, PEG$_{40kDa}$ dichloride was prepared by using a procedure similar to that reported for synthesizing mPEG$_{5k}$Cl, Greenwald et al. *J Org. Chem.*, 1995, 60, 331–336., the contents of which are incorporated herein by reference. A solution of the PEG$_{40kDa}$ dichloride in 40% methylamine (400 ml) was then placed in a sealed polypropylene bottle and heated at 60° C. for 3 days. Subsequent removal of the solvent from the reaction mixture followed by recrystallization from 2-propanol (1.5L) yielded 12 (44 g, 87%). $^{13}$C NMR (CDCl$_3$)δ: 33.10, 48.38, 66.18–71.60 (PEG).

EXAMPLE 11

PEG$_{40kDa}$amide of acid 10—Compound 14

Continuing with reference to FIG. 2, PEG$_{40kDa}$diamine hydrochloride 13 was prepared following a procedure similar to that reported for mPEG$_{5k}$NH$_2$ by Greenwald et al. *J.Org.Chem.*, 1995, 60, 331–336, (the contents of which were incorporated by reference supra). A mixture of 10, (0.14 g, 0.3 mmol), the PEG$_{40kDa}$diamine hydrochloride 13, (3.0 g, 0.075 mmol), DMAP (55 mg, 0.45 mmol), and DIPC (38 mg, 0.3 mmol) in anhydrous dichloromethane (30 ml) was stirred for 18 hours at room temperature. Removal of the solvent in vacuo and recrystallization from 2-propanol gave 14 (2.8 g, 90%).

$^{13}$CNMR(CDCl$_3$)δ: 168.39, 168.09, 166.51, 156.8, 151.80, 148.44, 146.22, 144.76, 131.04, 130.32, 129.17, 128.17, 127.91, 127.71, 119.77, 95.05, 76.72, 66.73–71.89 (PEG), 49.64, 38.24, 31.38, 7.17.

EXAMPLE 12 a) PEG$_{40kDa}$N-methylamide of acid 10—Compound 15

As shown in FIG. 2, a mixture of 10, (0.14 g, 0.3 nmmol), PEG$_{40kDa}$di-N-methylamine hydrochloride 13, (3.0 g, 0.075 mmol), DMAP (55 mg, 0.45 mmol), and DIPC (38 mg, 0.3 mmol) in anhydrous dichloromethane (30 ml) was stirred for 18 hours at room temperature. Removal of the solvent in vacuo and recrystallization from 2-propanol gave 15 (2.8 g, 90%).

$^{13}$C NMR(CDCl$_3$)δ: 168.73, 168.09, 166.51, 156.58, 151.80, 148.18, 145.91, 144.77, 130.84, 130.03, 128.95, 127.99, 127.71, 127.61, 127.40, 119.77, 95.05, 76.72, 66.46–71.65 (PEG), 49.41, 48.3, 47.5, 35.24, 33.3, 31.06, 6.97.

b) PEG$_{40kDa}$ ester of acid 10–Compound 44

Figure 13:
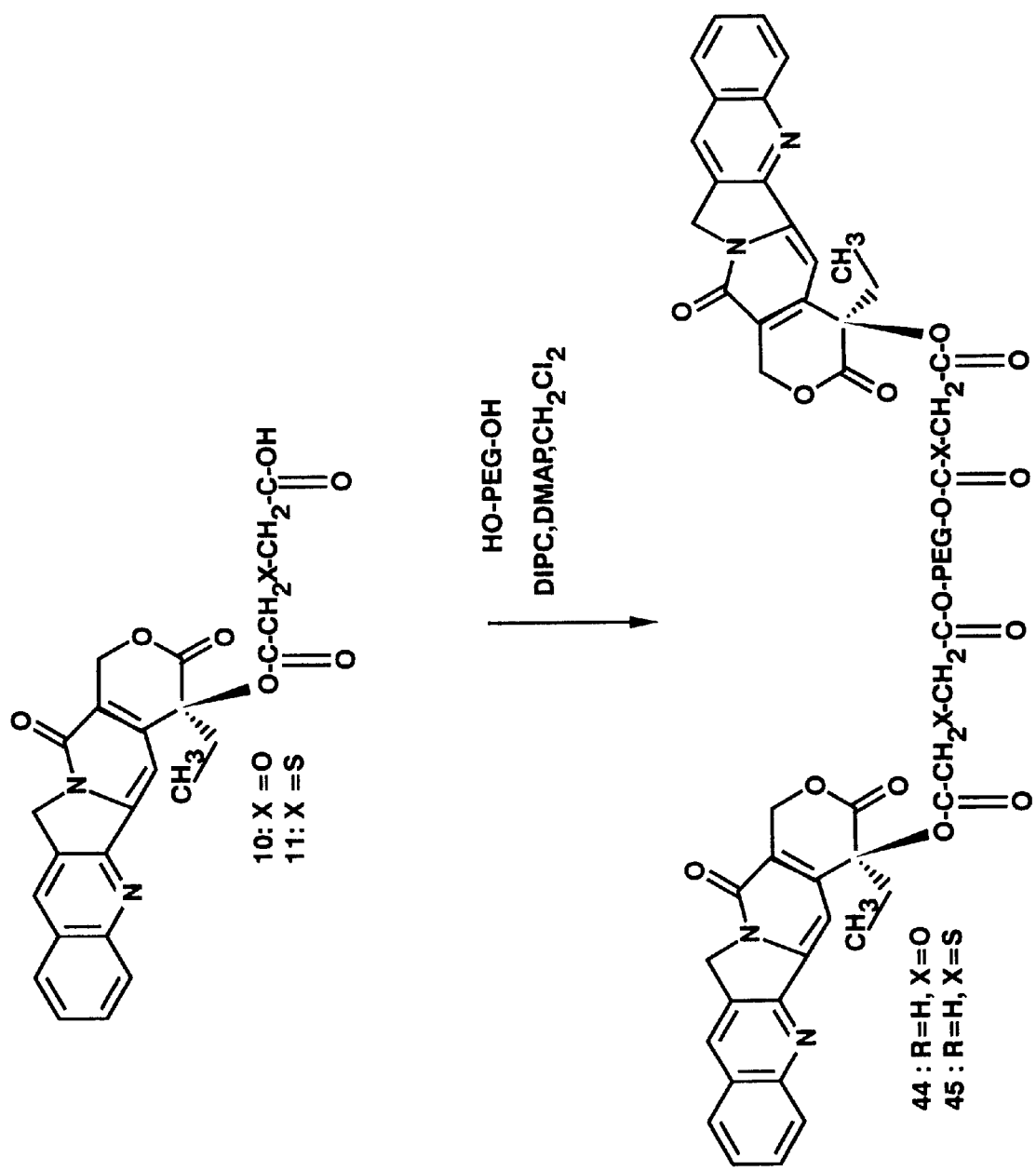
FIG. 13 is a schematic representation of the reactions carried out in accordance with Examples 12b and 15b.

Referring now to FIG. 13, a mixture of 10, (0.14 g, 0.3 mmol), PEG$_{40kDa}$dicarboxylic acid 43, see Example 22 infra, (3.0 g, 0.075 mmol), DMAP (55 mg, 0.45 mmol), and DIPC (38 mg, 0.3 mmol) in anhydrous dichloromethane (30 ml) was stirred for 18 hours at room temperature. Removal of the solvent in vacuo and recrystallization from 2-propanol gave 44 (2.8 g, 90%).

EXAMPLE 13

Mono t-Butyl ester of thiodiglycolic acid—Compound 7

As shown in FIG. 2, a solution of thiodiglycolic anhydride (10 g, 0.09 mol) and DMAP (10.5 g, 0.09 mol) in t-butanol (75ml) was stirred at reflux temperature for 18 hours. The solvent was removed under reduced pressure and the residue dissolved in water (100 ml). The aqueous solution was acidified to pH 2.5 to 3.0 with 1N HCl and extracted with dichloromethane. Removal of the solvents from the dried extracts yielded the mono t-butyl ester of thiodiglycolic acid 7. $^{13}$C NMR (CDCl$_3$)δ:174.55, 168.95, 81.83, 34.43, 33.00, 27.49, 21.23.

EXAMPLE 14

Camptothecin-20-O ester of 7–Compound 9

Continuing with reference to FIG. 2, a mixture of 7, (4.2 g, 0.02 mol), camptothecin (4.0 g, 0.01 mol), DMAP (2.7 g, 0.02 mol), and DIPC (2.8 g, 0.02 mol) in anhydrous dichloromethane (40 ml) was stirred for 18 hours at room temperature. The reaction mixture was then washed with water, saturated aqueous sodium bicarbonate, 0.1N HCl and finally with water. The organic layer was dried (anhyd.MgSO$_4$) and removal of the solvent in vacuo and recrystallization of the resultant residue from dichloromethane/ether gave 9.

$^{13}$C NMR (CDCl$_3$)δ: 168.81, 168.65, 167.10, 157.33, 152.25, 148.86, 146.35, 145.63, 130.84, 131.13, 130.62, 129.66, 128.41, 128.15, 128.02, 120.11, 95.86, 81.96, 76.53, 67.03, 49.95, 34.27, 32.87, 31.67, 27.94, 7.57.

EXAMPLE 15

Camptothecin-20-O-mono ester of thiodiglycolic acid—Compound 11

As shown in FIG. 2, compound 9 (0.8 g, 1.5 mmol) in dichloromethanetrifluroacetic acid solution (12 ml, 8:4) was stirred at room temperature for 30 minutes. The solvent was removed under reduced pressure, and the resulting solid was recrystallized from dichloromethane/ether to yield 11.

EXAMPLE 16 a) PEG$_{40kDa}$amide of acid 11—Compound 16

A mixture of 11, (0.14 g, 0.3 mmol), PEG$_{40kDa}$diamine hydrochloride 13, (3.0 g, 0.075 mmol), DMAP (55 mg, 0.45 mmol), and DIPC (38 mg, 0.3 mmol) in anhydrous dichloromethane (30 ml) was stirred for 18 hours at room temperature. Removal of the solvent in vacuo and re-crystallization of the solid product was accomplished from 2-propanol to give 16. See FIG. 2.

b) PEG$_{40kDa}$ ester of acid 11—Compound 45

Referring now to FIG. 13, a mixture of 11, (0.14 g, 0.3 mmol), PEG$_{40kDa}$diol, see Example 22 infra, (3.0 g, 0.075 mmol), DMAP (55 mg, 0.45 mmol), and DIPC (38 mg, 0.3 mmol) in anhydrous dichloromethane (30 ml) was stirred for 18 hours at room temperature. Removal of the solvent in vacuo and recrystallization of the solid product was accomplished from 2-propanol to give 45.

EXAMPLE 17

PEG$_{40kDa}$N-methylamide of acid 11—Compound 17

A mixture of 11, (0.14 g, 0.3 mmol), PEG$_{40kDa}$di-N-methylamine hydrochloride 12, (3.0 g, 0.075 mmol), DMAP (55 mg, 0.45 mmol), and DIPC (38 mg, 0.3 mmol) in anhydrous dichloromethane (30 ml) was stirred for 18 hours at room temperature. Removal of the solvent in vacuo and recrystallization from 2-propanol gave 17. See FIG. 2.

EXAMPLE 18

PEG$_{40kDa}$thioacetic Acid 18

Figure 3:
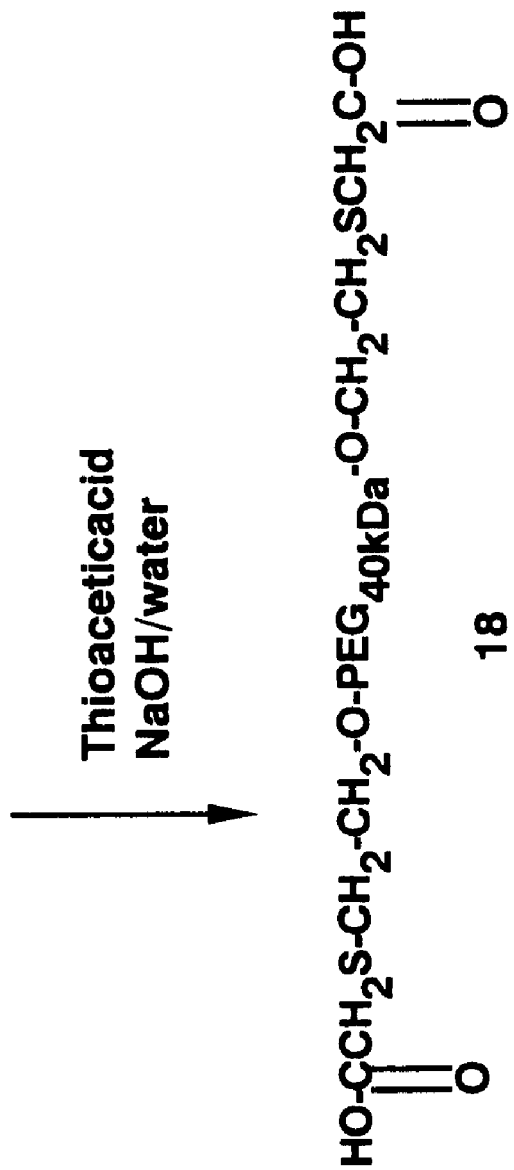
FIG. 3 is a schematic representation of the reaction carried out in accordance with Example 18.

Referring now to FIG. 3, a mixture of of PEG$_{40kDa}$ dichloride, (40.0 g, 1 mmol), ref. Greenwald et al. J.Org.Chem., 1995, 60, 331–336), thioacetic acid (3.6 g, 40 mmol) and sodium hydroxide (4.0 g, 40 mmol) in water (160 ml) was placed in a sealed polyethylene bottle and placed in a water bath at 70° C. for 18 hours. The reaction mixture was cooled to room temperature, diluted with 100 ml of water and acidified with hydrochloric acid to pH 2.0, followed by extraction with methylene chloride. The combined extracts were dried over magnesium sulfate, filtered, and the solvent removed by rotary evaporator. The solid residue was recrystallized from 2-propanol to yield 35 g (69%) of product. $^{13}$C NMR (CDCl$_3$)δ:31.17, 33.23, 58.24, 170.66.

EXAMPLE 19

Camptothecin-20-O-ester of 18—compound 19

Figure 4:
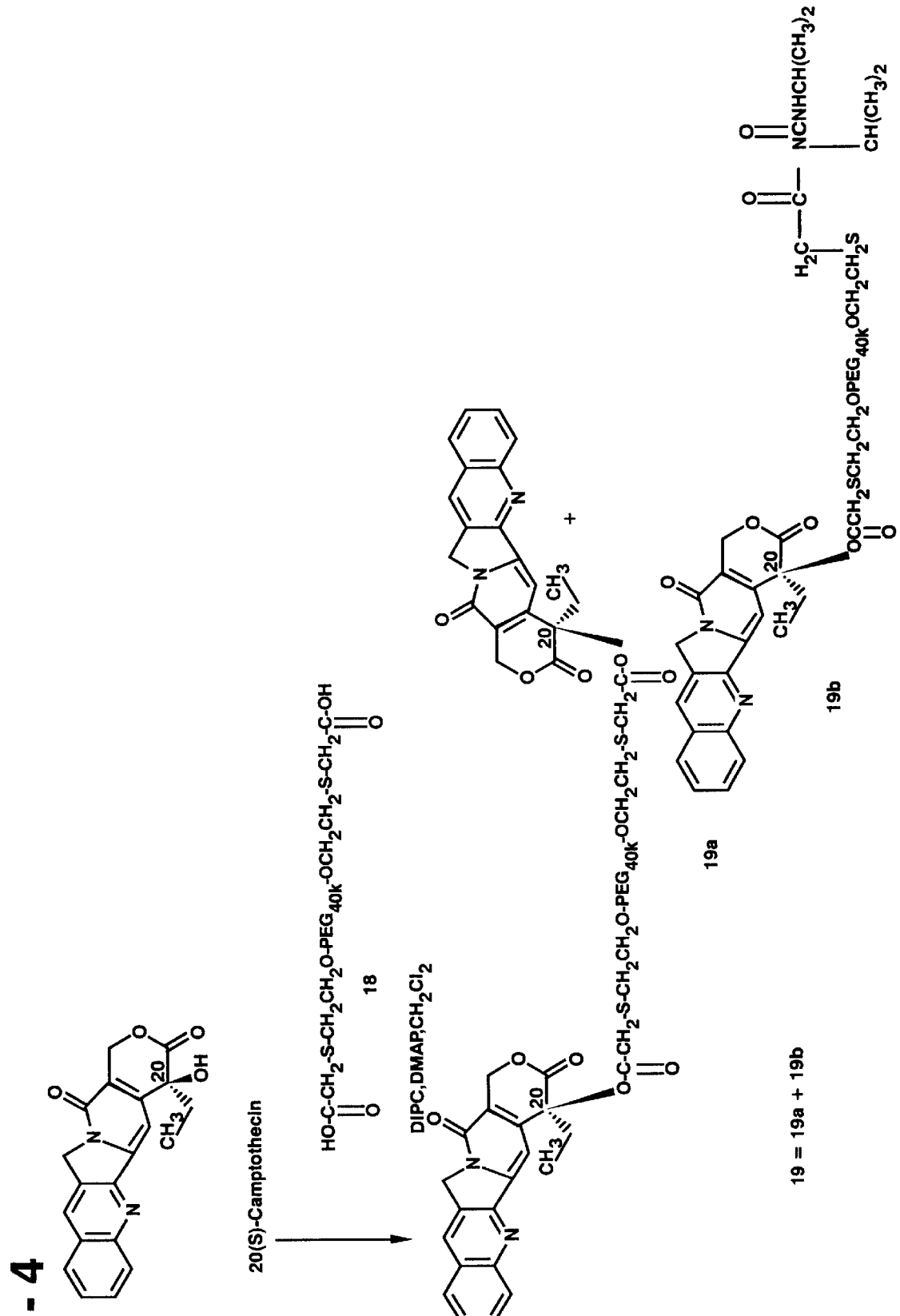
FIG. 4 is a schematic representation of the reaction carried out in accordance with Example 19.

Referring now to FIG. 4, PEG$_{40kDa}$ thioacetic acid (18, 16 g, 0.40 mmol) was dissolved in 250 mL of anhydrous methylene chloride at room temperature. To this solution, DIPC (280 mg, 2.2 mmol), DMAP (280 mg, 2.2 mmol) and camptothecin (800 mg, 2.2 mmol) were added at 0° C. The reaction mixture was allowed to warm to room temperature and left for 16 hours followed by removal of the solvent in vacuo. The residue was recrystallized from 2-propanol to yield 13.6 g, 77%. The product was found to be a mixture of 19a+19b.

EXAMPLE 20

Paclitaxel-2'-O-ester of 18—Compound 20

Figure 5:
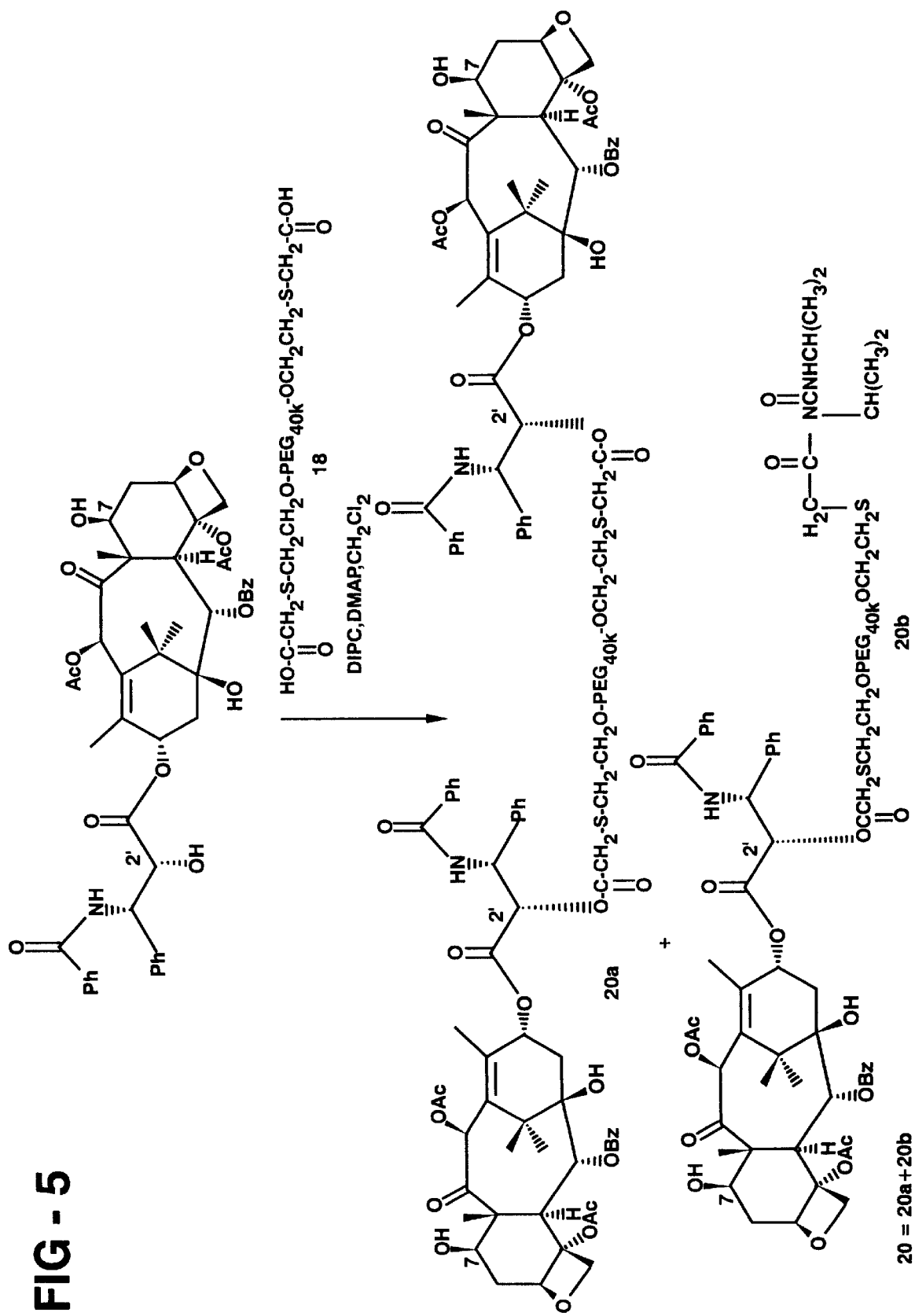
FIG. 5 is a schematic representation of the reactions carried out in accordance with Example 20.

Referring now to FIG. 5, PEG$_{40kDa}$thioacetic acid (18, 8 g, 0.20 mmol) was dissolved in 120 mL of anhydrous methylene chloride at room temperature. To this solution, DIPC (108 μL, 0.70 mmol), DMAP (86 mg, 0.70 mmol) and paclitaxel (606 mg, 0.70 mmol) were added at 0° C. The reaction mixture was allowed to warm to room temperature and left for 16 hours. The solution was washed with 0.1N HCl, dried and evaporated under reduced pressure to yield a white solid (15 g, 80%) which was recrystallized from 2-propanol. The product was found to be a mixture of 20a+20b.

$^{13}$C NMR (CDCl$_3$)δ: 8.59, 13.60, 19.62, 19.70, 20.92, 21.0, 21.29, 21.65, 25.66, 30.34, 30.72, 31.92, 34.82, 41.86, 42.13, 44.74, 44.81, 47.32, 52.07, 57.15, 66.36–71.13 (PEG), 73.66, 73.95, 74.36, 74.4, 79.89, 83.23, 126.19, 126.43, 126.77, 126.82, 127.42, 127.68, 127.79, 127.96, 128.59, 129.04, 129.22, 130.68, 131.95, 132.51, 132.89, 136.05, 140.99, 152.57, 165.29, 166.29, 166.98, 168.73, 169.44, 202.33.

EXAMPLE 21 a) Camptothecin-20-O-(l)Alanate TFA salt (23)

Referring now to FIG. 6, tBoc-l-Alanine (1.8 g, 9.39 mmol) was dissolved in 700 mL of anhydrous methylene chloride at room temperature. To this solution, DIPC (1.5 ml 9.39 mmol), DMAP (765 mg, 6.26 mmol) and camptothecin (1.09 g, 3.13 mmol) were added at 0° C. The reaction mixture was allowed to warm to room temperature and left for 16 hours. The solution was washed with 0.1N HCl, dried and evaporated under reduced pressure to yield a white solid which was recrystallized from methanol to give Camptothecin-20-O-ester of t-Boc-l-Alanine 21. $^1$HNMR (DMSO-D$_6$): δ0.9(t), 1.3(d). 1.6(s), 2.1(m), 4(m), 5.3(s), 5.5(s), 7.3(s), 7.5–8.8(m).

b) Compound 21 (1.19 g, 2.12 mmol) was dissolved in a mixture of methylene chloride (15 ml) and trifluoroacetic acid (15 ml) and stirred at room temperature for 1 hour. The solvent was removed and the solid was recrystallized from methylene chloride and ether to give (1 g) of product 23 as the TFA salt.

$^1$HNMR(DMSO-D$_6$)δ:1.0(t), 1.6(d), 2.2(m), 4.4(m), 5.4 (s), 5.6(s), 7.2(s), 7.7–8.8(m).

$^{13}$C NMR (DMSO-D$_6$)δ: 7.5, 15.77, 30.09, 47.8, 50.27, 66.44, 77.5, 94.92, 119.10, 127.82, 128.03, 128.62, 128.84, 129.75, 130.55, 131.75, 144.27, 146.18, 147.90, 152.24, 156.45, 166.68, 168.69.

c) Camptothecin-20-O-(d/l) Alan ate TFA salts

The d-alanate and d/l racemic alanate were prepared using the same procedures outline above with the respective isomer replacing the tBoc-l-alanate used in Example 21 a).

d) Camptothecin-20-O-Glycinate, TFA salt—Compound 47

Figure 14:
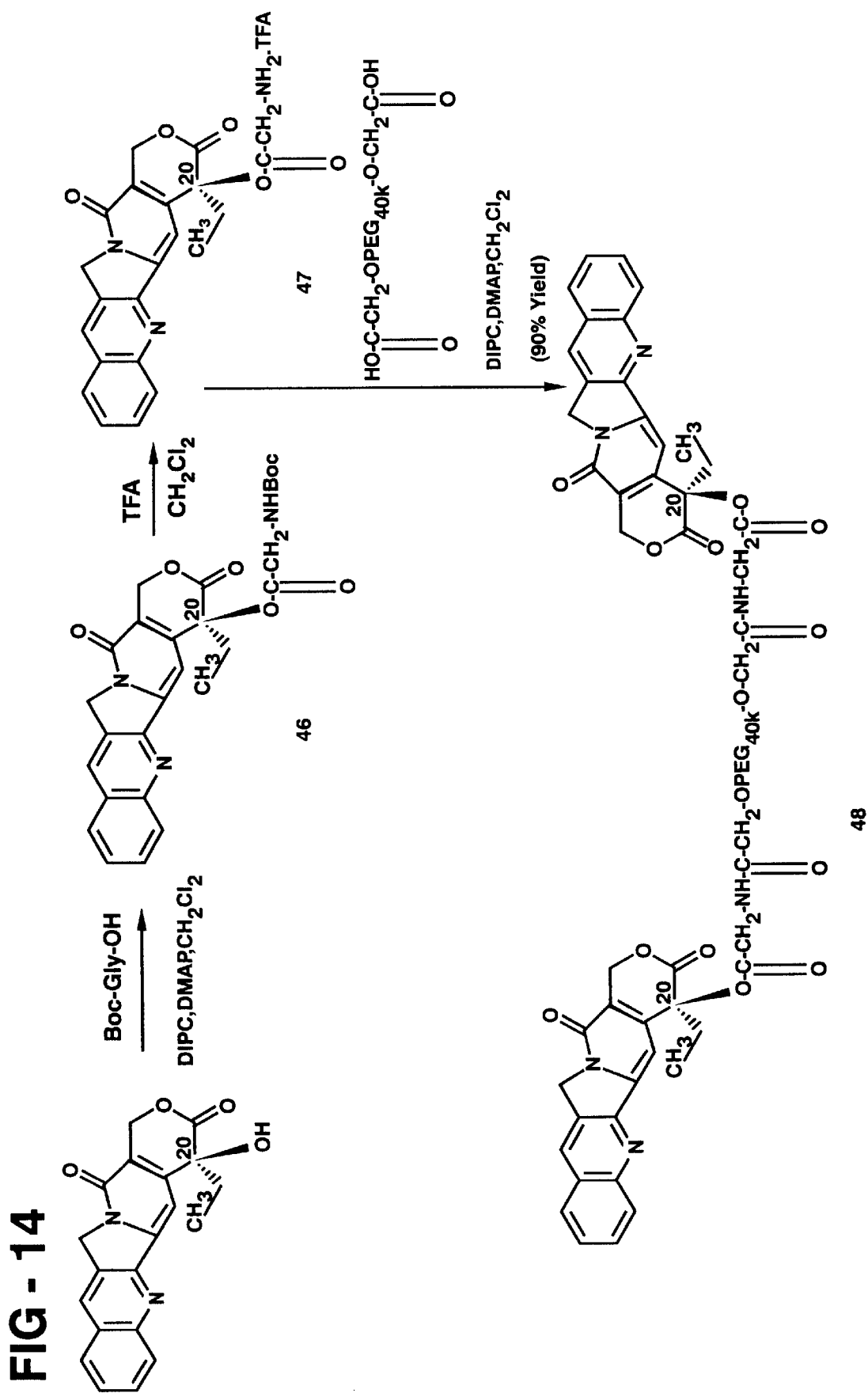
FIG. 14 is a schematic representation of the reactions carried out in accordance with Examples 21d and 22 IIb.

Referring now to FIG. 14, it can be seen that the camptothecin-20-O-glycinate was prepared using a procedure similar to Example 21 a) above with the tBoc-glycinyl camptothecin (46) replacing the t-Boc-l-alanyl camptothecin (21) to give 47.

e) 10,11-Methylenedioxycamptothecin 20-O-glycinate TFA salt

The process of Example 21, steps a)–d) are repeated using 10,11-methylenedioxycamptothecin to form the 20-O-alanate, and the glycinate TFA salt.

EXAMPLE 22

Camptothecin-20-O-ester of PEG$_{40kDa}$L-Alanine—Compound 25

Method A

I) PEG (40 kDa) dicarboxylic acid a) Di-t-BUTYL ESTER OF PEG (40,000) DI-CARBOXYLIC ACID A solution of 50 grams (1.3 mmoles) of PEG-(OH)$_2$ in 750 ml of toluene was azeotroped with the removal of 150 ml of distillate. The reaction mixture was then cooled to 30° C., followed by the addition of 4 ml (4.0 mmoles) of a 1.0 molar solution of potassium t-butoxide in t-butanol. The resulting mixture was stirred for 1 hour at room temperature, followed by the addition of 1.6 grams (8.0 mmoles) of t-butylbromoacetate. The resulting cloudy mixture was heated to reflux, followed by removal of the heat, and stirring for 18 hours at room temperature. The reaction mixture was filtered through celite and the solvent removed by rotary evaporator. The residue was recrystallized from methylene chloride/ethyl ether to yield 45.2 grams (86% yield). The named product, however was found to be over 99% pure, the starting material being present in an amount of less than 1.0%. $^{13}$CNMR assignments: (CH$_3$)$_3$C, 27.7 ppm; (CH)$_3$C, 80.9 ppm; C=O, 169.1 ppm.

b) PEG (40,000) DI-CARBOXYLIC ACID

A solution of 20.0 grams (0.5 mmoles) of PEG (40,000) carboxylic acid t-butyl ester, 100 ml of trifluoroacetic acid, and 0.1 ml of water in 200 ml of methylene chloride was stirred at room temperature for 3 hours. The solvent was then removed by rotary evaporation, followed by recrystallization of the residue from methylene chloride/ethyl ether to yield 16.9 grams (84% yield) of product. Purity of the named product was confirmed to be in excess of 99%. $^{13}$CNMR assignments: C=O, 170.9 ppm.

II a) Synthesis of the Camptothecin-20-O-Alanate PEG Derivative

Referring to FIG. 6, PEG$_{40kDa}$ diacid (6.5 g, 0.62 mmol) was dissolved in 60 mL of anhydrous methylene chloride at room temperature and to this solution at 0° C. were added DIPC (148 μL, 0.97 mmol), DMAP (296 mg, 2.43 mmol) and compound 23 (627 mg, 0.97 mmol). The reaction mixture was allowed to warm to room temperature and left for 16 hours. The solution was washed with 0.1N HCl, dried and evaporated under reduced pressure to yield 25 as a white solid which was recrystallized from 2-propanol (5.5 g, 83.%). $^{13}$C and $^1$H NMR analysis confirmed the structure. $^{13}$C NMR (CDCl$_3$)δ6.81, 16.93, 30.80, 46.59, 49.28, 66.17, 69.77, 70.2–71 (PEG),76.53, 94.79, 119.20, 127.18, 127.53, 127.91, 128.95, 129.72, 130.68, 144.58, 145.76, 148.05, 151.46, 156.37, 165.99, 168.87, 170.32.

The procedure of IIa) was repeated using propane phosphonic acid cyclic anhydride (PPACA) in place of DIPC in order to form the named compound.

The racemic mixture is prepared in the same manner.

II b) Synthesis of the Camptothecin-20-O-Glycinate PEG$_{40kDa}$-Amide Derivative—Compound 48

Referring now to FIG. 14, the camptothecin-20-O-ester of PEG$_{40kDa}$glycinate was prepared using a procedure similar to that illustrated in Example 22a with compound 47 (FIG. 14) replacing compound 23 (FIG. 6) in order to provide compound 48

III) Analysis of Camptothecin 20-O-ester of PEG$_{40kDa}$ l-Alanine(25)

The UV absorbance of native camptothecin in methylene chloride was determined at 227 nm for five different concentrations ranging from 4 to 21 μM. From the standard plot of absorbance vs. concentration, the absorption coefficient for camptothecin was calculated to be 2.96×10$^4$ Mol$^{-1}$Cm$^{-1}$. Camptothecin compound 25 was dissolved in methylene chloride at an approximate concentration of 4 μM, and the UV absorbance of this compound at 227 nm was determined. Using this value, and employing the absorption coefficient obtained from above, the concentration of camptothecin in the sample was determined. Thus, dividing this value by the camptothecin-PEG ester concentration provided the percentage of camptothecin in the esters.

Determination of % of camptothecin in the product using the UV method indicated 2 eq. of camptothecin per PEG molecule.

IV) Synthesis of the Camptothecin-20-O-Glycinate PEG$_{40kDa}$ Carbamate Derivative—Compound 49

Figure 15:
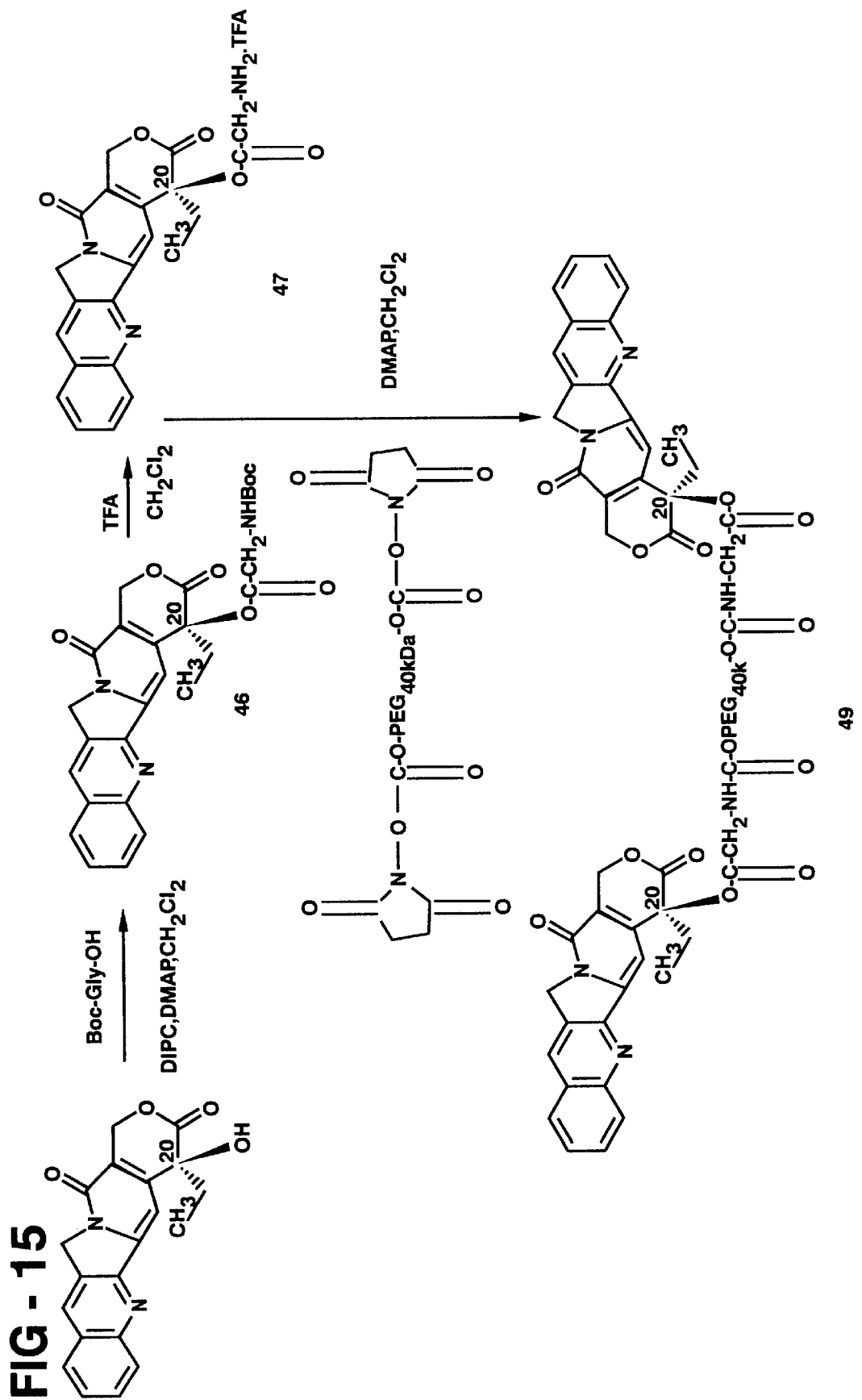
FIG. 15 is a schematic representation of the reactions carried out in accordance with Example 22, Method A step IV.
Figure 16:
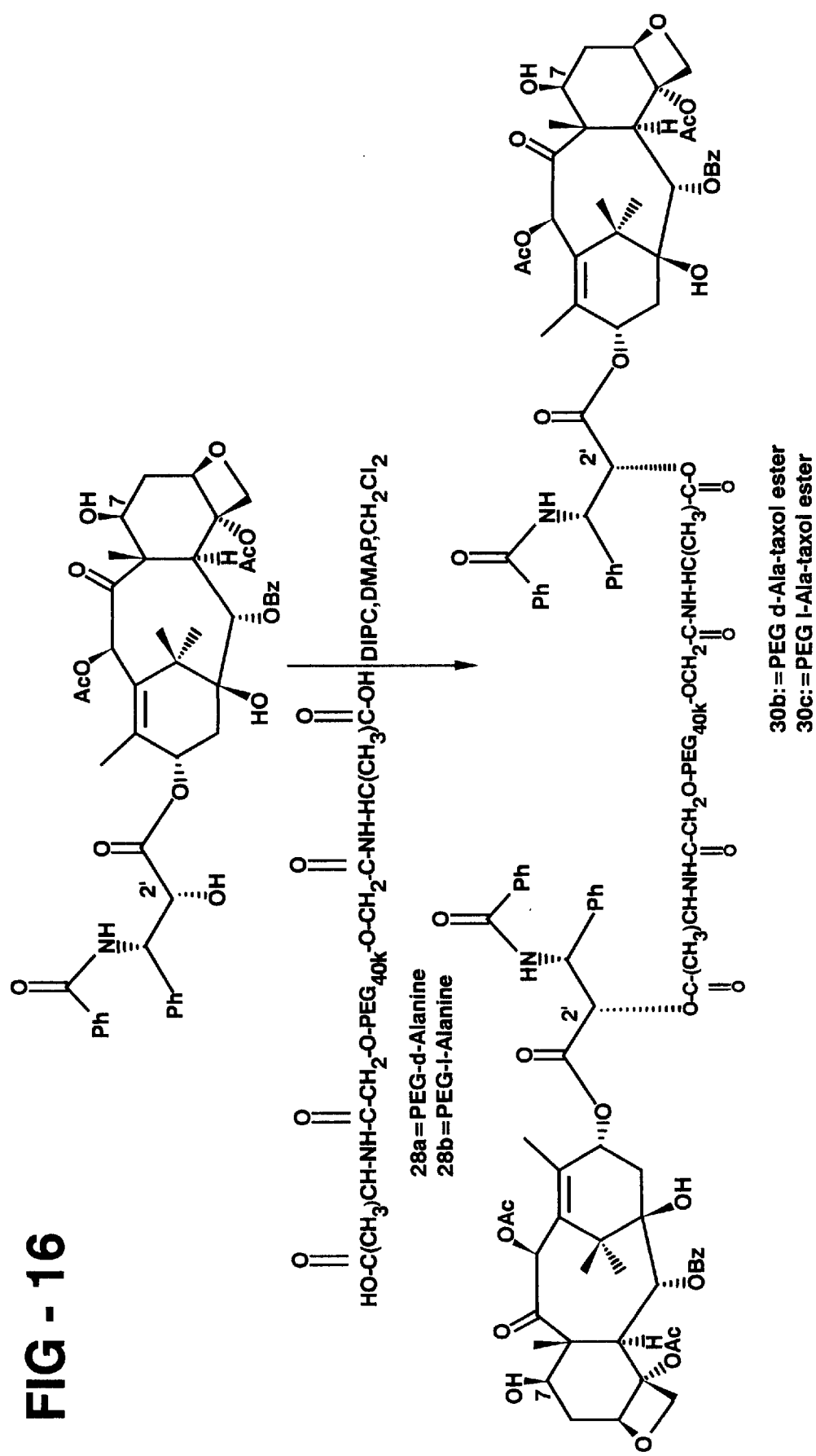
FIG. 16 is a schematic representation of the reactions carried out in accordance with Examples 29b and 29c.
Figure 17:
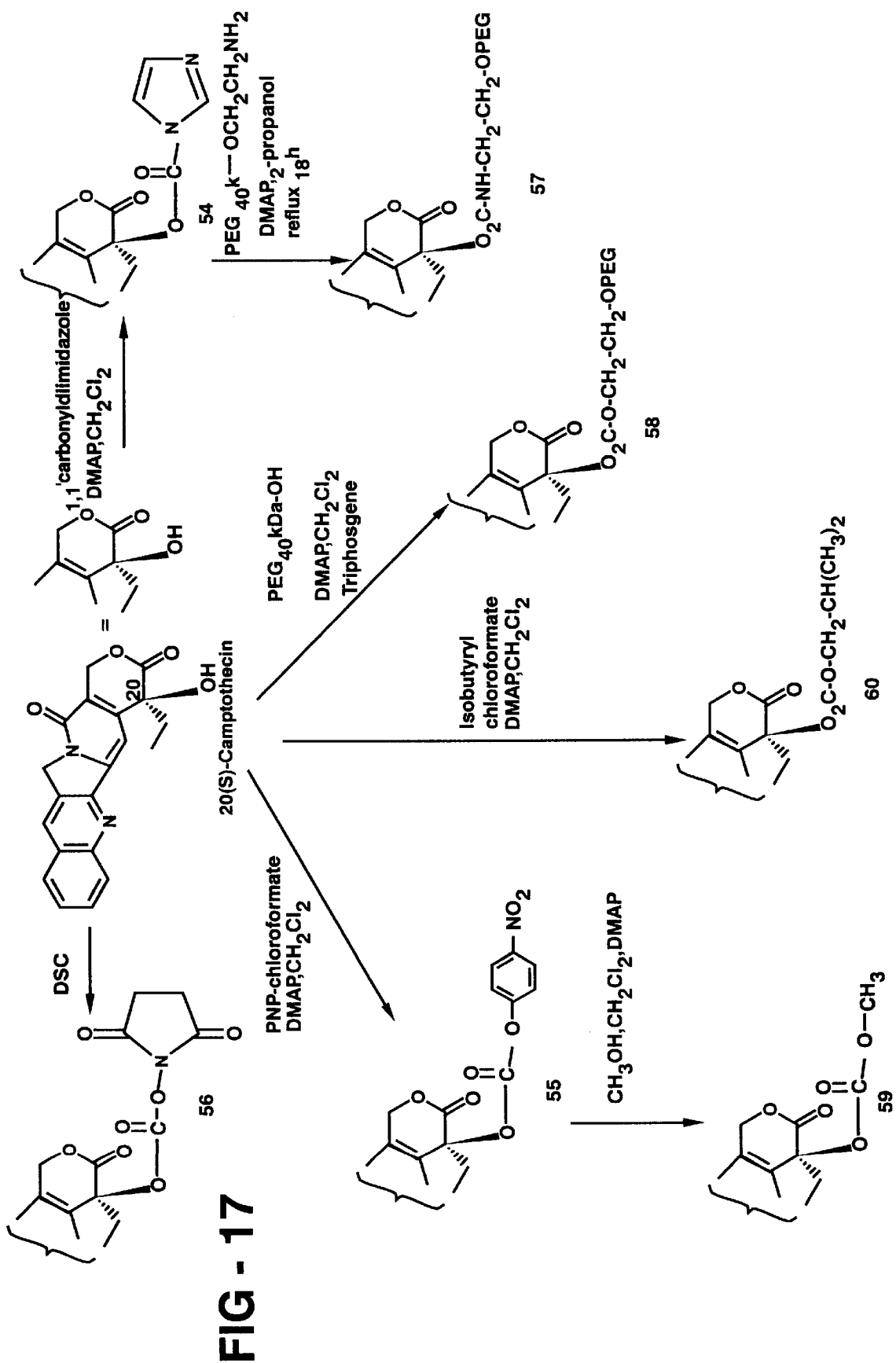
FIG. 17, is a schematic representation of the reactions carried out in accordance with Examples 47 through 53.

Referring now to FIG. 15, PEG$_{40kDa}$ di-SC-PEG (2.0 g, 0.59 mmol) prepared according to the method described in U.S. Pat. No. 5,122,614, the contents of which are incorporated herein by reference, was dissolved in 40 mL of anhydrous chloroform at room temperature. To this solution was added DMAP (60.7 mg, 0.5 mmol) and compound 47 (122 mg, 0.2 mmol). The reaction mixture was allowed to warm to room temperature and left for 16 hours. The solution was washed with 0.1N HCl, dried and evaporated under reduced pressure to yield the title compound 49 as a white solid which was recrystallized from 2-propanol.

EXAMPLE 23

Camptothecin-20-O-ester of PEG$_{40kDa}$(d/l)-Alanine—Compound 25

Method B

Referring now to FIG. 9 for guidance, compound 25 can also be prepared using a similar procedure to that shown below in Example 30 in order to prepare compound 31, substituting PEG-d-alanine 28, or PEG-l-alanine 29 (shown in FIG. 7) in place of 27.

EXAMPLE 24

Camptothecin-20-O-ester of PEG$_{40kDa}$(d)-Alanine—Compound 26

Method A

As shown in FIG. 6, the title compound is prepared in a similar manner as that used for preparing compound 25 in Example 22 using tBoc-d-Alanine as starting material.

EXAMPLE 25

Camptothecin-20-O-ester of PEG$_{40kDa}$(d)-Alanine—Compound 26

Method B

Compound 26 is also prepared using a similar procedure to that described in Example 30 for preparing compound 31 and substituting PEG-d-Alanine 29 (See FIG. 7) in place of 27. The racemic alanine mixture can also be prepared using either of the foregoing procedures.

EXAMPLE 26

PEG$_{40kDa}$-β-Alanine(27)

Figure 7:
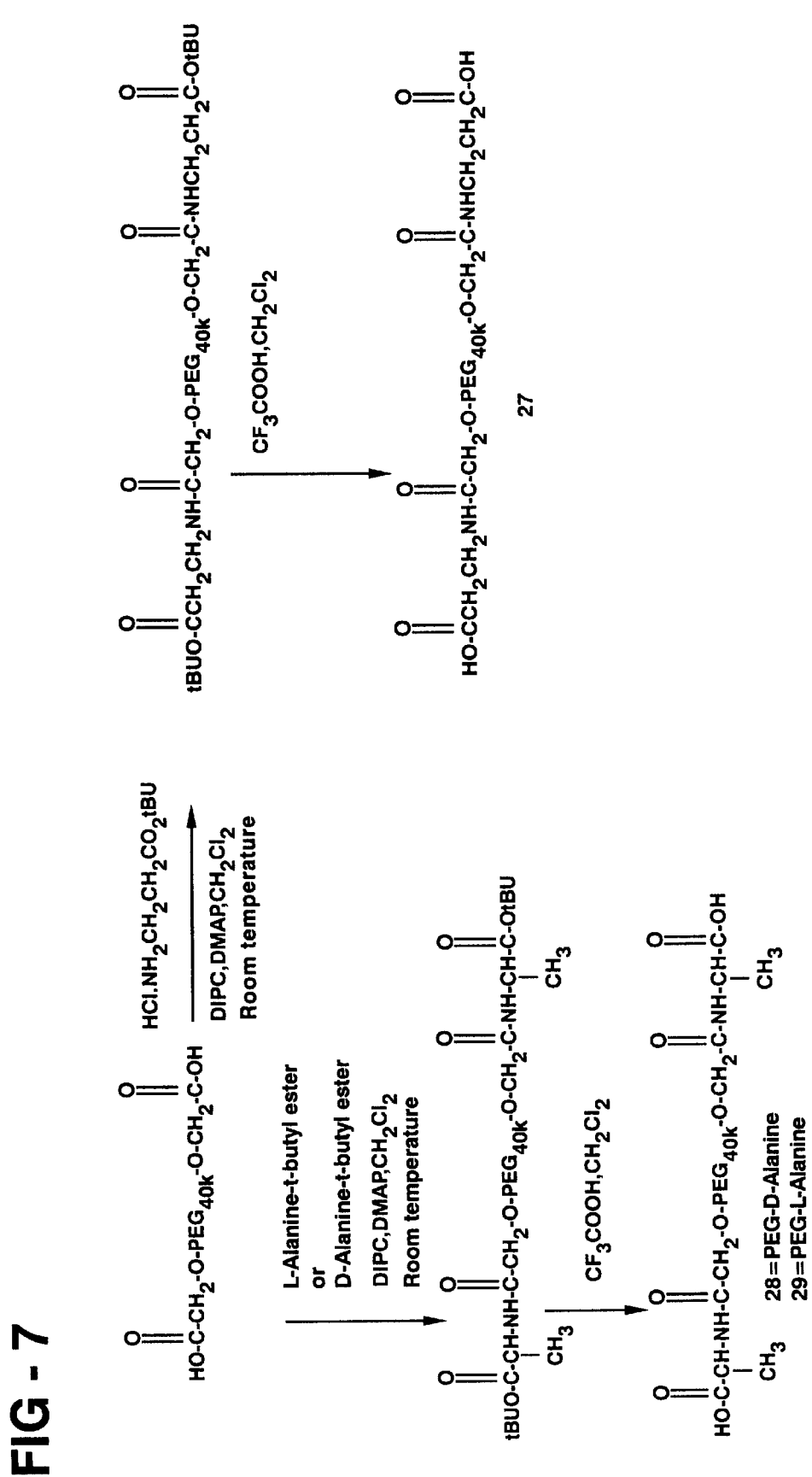

As shown in FIG. 7, PEG$_{40kDa}$ diacid (3 g, 0.075 mmol) was dissolved in 30 mL of anhydrous methylene chloride at room temperature. To this solution at 0° C. were added DIPC (91.4 μL 0.72 mmol), DMAP (128 mg, 1.04 mmol) and β-alanine-t-butylester (109 mg, 0.59 mmol). The reaction mixture was allowed to warm to room temperature after 3 hours and left for 16 hours. The solution was washed with 0.1N HCl, dried and evaporated under reduced pressure to yield PEG$_{40kDa}$β-alanine- t-butyl ester as a white solid which was dissolved in a mixture of methylene chloride (50 ml) and trifluoroacetic acid (25 ml) at 0° C. for overnight. Solvent was removed and the solid was recrystallized from methylene chloride/ether to give 27 (2.3 g, 77%).

$^{13}$CNMR (CDCl$_3$)δ: 32.99, 33.62, 68.10, 69.72, 169.08, 172.04.

EXAMPLE 27

PEG$_{40kDa}$-d-Alanine(28)

As shown in FIG. 7, the title compound is prepared by using a similar procedure to that used for synthesizing compound 27 in Example 26, substituting (d)-alanine-t-butyl ester in place of β-alanine-t-butyl ester.

EXAMPLE 28

PEG$_{40kDa}$-l-Alanine(29)

The title compound is prepared by using a similar procedure to that used for synthesizing compound 27 in Example 26, substituting (l)-alanine-t-butyl ester in place of β-alanine-t-butyl ester. (See FIG. 7).

EXAMPLE 29 a) Paclitaxel-2'-O-ester of 27—Compound 30a

Figure 8:
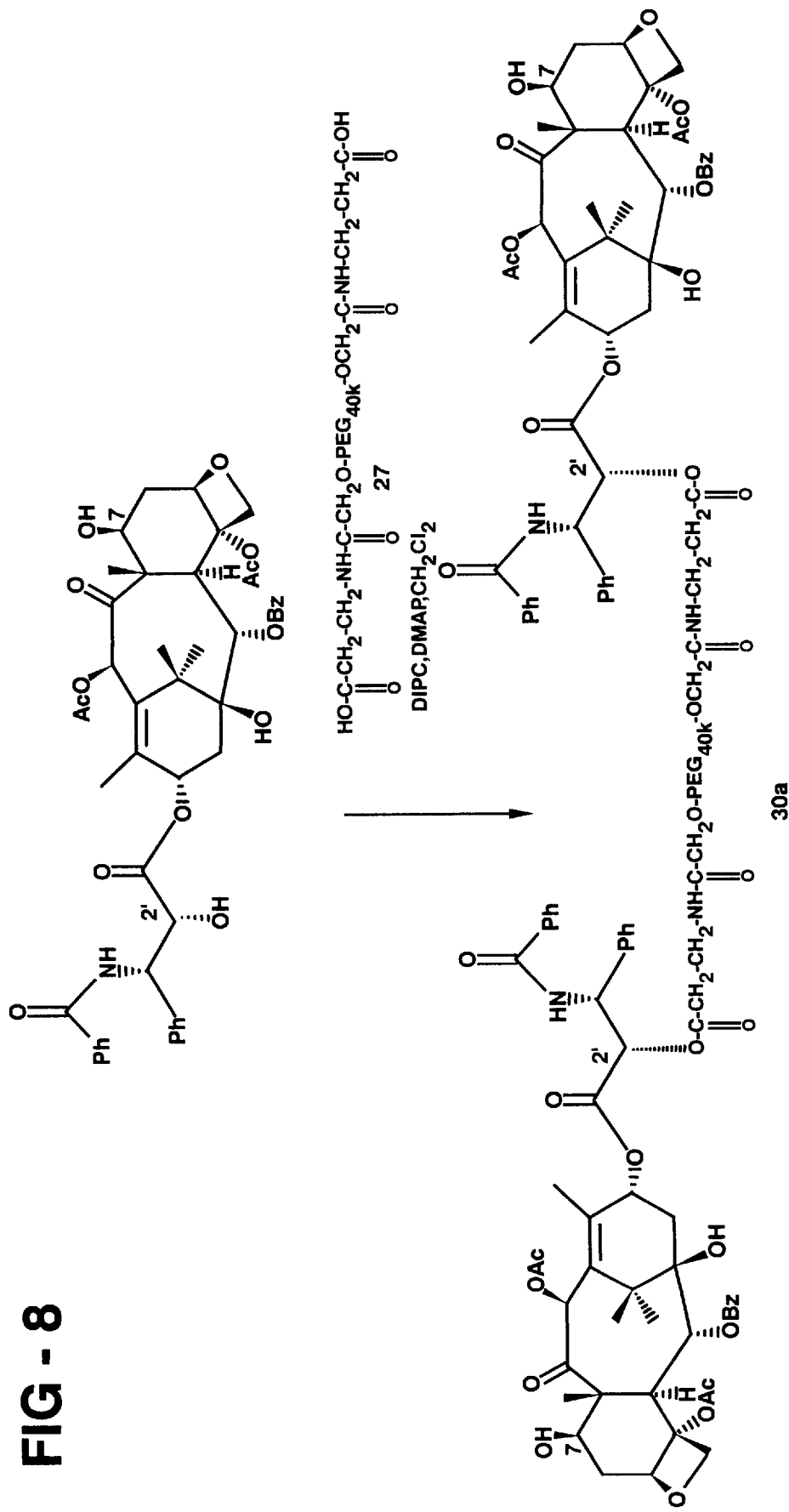
FIG. 8 is a schematic representation of the reaction carried out in accordance with Example 29.

Referring to FIG. 8, PEG$_{40kDa}$ β-alanine (27, 2.3 g, 0.057 mmol) was dissolved in 20 mL of anhydrous methylene chloride at room temperature. To this solution at 0° C. were added DIPC (32 μL, 0.2 mmol), DMAP (25 mg, 0.2 mmol) and paclitaxel (175.6 mg, 0.2 mmol). The reaction mixture was allowed to warm to room temperature and left for 16 hours. The solution was washed with 0.1N HCl, dried and evaporated under reduced pressure to yield 30a as a white solid (2 g, 87%) which was recrystallized from 2-propanol.

$^{13}$CNMR(CDCl$_3$)δ:9.08, 14.22, 21.49, 21.89, 22.18, 25.9, 33.55, 34.90, 35.03, 35.21, 42.67, 46.9, 52.22, 57.51, 67.59–71.96 (PEG), 73.97, 74.60, 75.01, 80.11, 83.52, 126.32, 127.11, 127.57, 128.05, 128.17, 128.65, 129.50, 130.79, 131.96, 133.06, 136.75, 141.84, 165.97, 166.77, 167.45, 169.21, 169.70, 170.28, 170.33, 202.82.

b) Paclitaxel-2'-O-ester of 28—Compound 30b

The procedure of Example 29a was repeated using d-alanine instead of β-alanine to yield compound 30b.

c) Paclitaxel-2'-O-ester of 29—Compound 30c

The procedure of Example 29a was repeated using l-alanine instead of β-alanine to yield compound 30c.

EXAMPLE 30

Camptothecin 20-O-ester of 27—Compound 31

Referring now to FIG. 9, PEG$_{40kDa}$ β-alanine(27, 2.3 g, 0.057 mmol) is dissolved in 20 mL of anhydrous methylene chloride at room temperature and to this solution at 0° C. are added DIPC (32 μL, 0.2 mmol), DMAP (25 mg, 0.2 mmol) and camptothecin (130 mg, 0.25 mmol). The reaction mixture is allowed to warm to room temperature and left for 16 hours. The solution is washed with 0.1N HCl, dried and evaporated under reduced pressure to yield 31.

EXAMPLE 31

Podophyllotoxin-4-O-ester of 27—Compound 32

Figure 10:
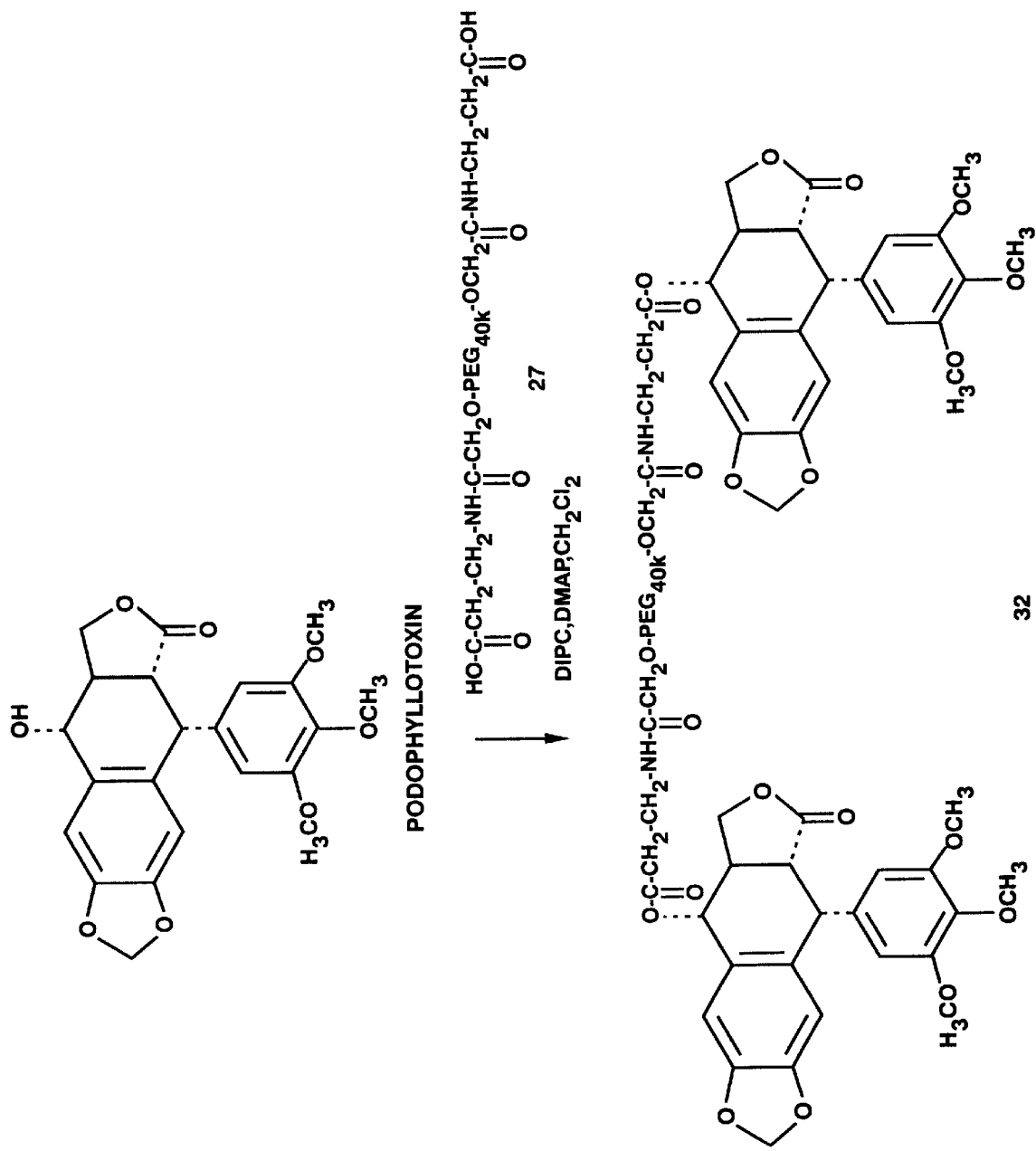
FIG. 10 is a schematic representation of the reaction carried out in accordance with Example 31.

Referring now to FIG. 10, PEG$_{40kDa}$ β-alanine (27, 2.3 g, 0.057 mmol) is dissolved in 20 mL of anhydrous methylene chloride at room temperature. To this solution at 0° C. are added DIPC (27.3 μL, 0.18 mmol), DMAP (21.9 mg, 0.18 mmol) and podophyllotoxin (110 mg, 0.25 mmol). The reaction mixture is allowed to warm to room temperature and left for 16 hours. The solution is washed with 0.1N HCl, dried and evaporated under reduced pressure to yield 32 as a white solid which is recrystallized from 2-propanol.

EXAMPLE 32

Camptothecin-20-O-ester of bromoacetic acid—Compound 35

Figure 11:
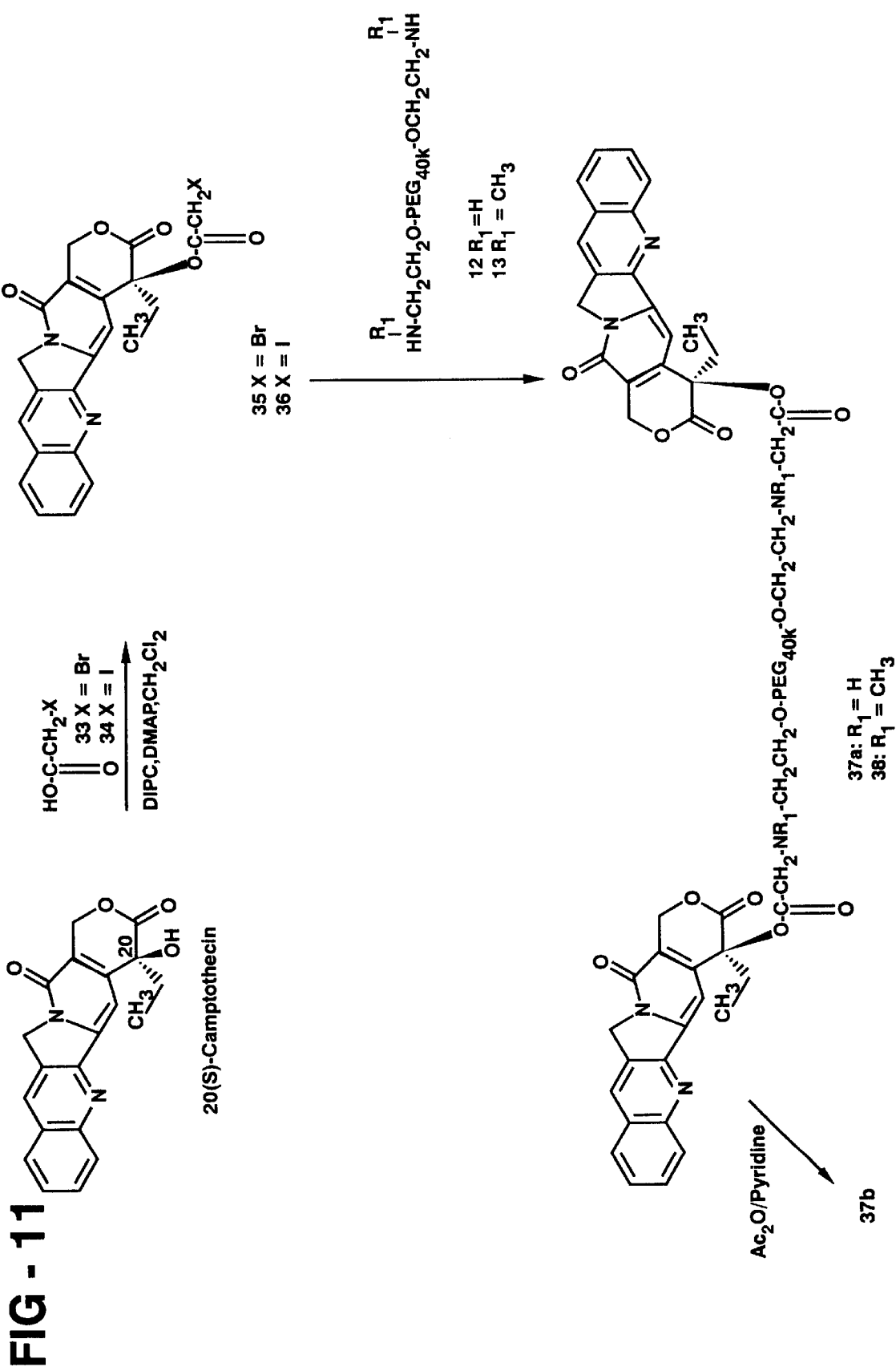
FIGS. 11 and 12 are schematic representations of the reactions carried out in accordance with Examples 32–39.

Referring to FIG. 11, to a suspension of camptothecin, (1.0 g,2.87 mmol) in CH$_2$Cl$_2$ (700 ml) was added bromoacetic acid (33, 1.2 g,8.61 mmol, Aldrich) diisopropylcarbodiimide (1.3 ml, 8.61 mmol) and dimethylaminopyridine (DMAP,700 mg, 5.74 mmo) at 0° C. Stirring was continued for 4 hours. The resulting yellow solution was concentrated to about 100 ml and washed with 1N hydrochloric acid (10 ml×2), followed by 1% aqueous sodium bicarbonate solution (10 ml×2). The organic layer was dried (anhyd.MgSO$_4$) and evaporated in vacuo to give a yellow solid which was recrystallized from ethyl acetate. The product was then triturated with methanol (10 ml), and the slurry filtered to yield 35 (0.9 g,67%).

$^1$H NMR(CDCl$_3$)δ 1.0(t),1.84(s),2.1–2.3(m),3.9–4.4(q), 5.28(s),5.4–5.8(dd), 7.2(s), 7.27(s),7.6–7.7(m).7.81–7.87 (m)7.92–7.95(d),8.19–8.22(d),8.39(s).

$^{13}$C NMR (CDCl$_3$)δ 7.52, 24.97, 31.77, 49.97, 67.16, 76.53, 95.73, 120.29, 128.05, 128.17, 128.39, 129.64, 130.65, 131.17, 144.94, 146.48, 148.84, 152.18, 157.24, 165.97, 166.83.

EXAMPLE 33

Camptothecin-20-O-ester of Iodoacetic acid—Compound 36

Continuing to refer to FIG. 11, iodoacetic acid (34, 1.7 g, 9.13 mmol, Aldrich) diisopropylcarbodiimide (1.4 ml,9.13 mmol) and dimethylaminopyridine (DMAP,743 mg, 8.04 mmo) was added to a suspension of camptothecin,(1.06 g,3.04 mmol) in CH$_2$Cl$_2$ (500 ml) at 0° C. Stirring was continued for 2 hours followed by 16 hours at room temperature. The resulting dark brown solution was concentrated to about 100 ml and washed with 1N hydrochloric acid (10 ml×2), followed by 1% aqueous sodium bicarbonate solution (10 ml×2). The organic layer was dried (anhyd.MgSO$_4$) and evaporated in vacuo to give a yellow solid which was recrystallized from ethyl acetate. The product was then triturated with methanol (10 ml), and the slurry filtered to yield 36 (1.3 g,80%).

$^1$H NMR(CDCl$_3$)δ 1.0(t),2.1–2.3(m),3.3 (s),3.9–4.4(q), 5.28(s),5.4–5.8(dd), 7.2(s), 7.27(s),7.6–7.7(m).7.81–7.87 (m)7.92–7.95(d),8.19–8.22(d),8.39(s).

$^{13}$C NMR(CDCl$_3$)δ 7.52, 31.77, 49.97, 67.16, 76.53, 95.73, 120.29, 128.05, 128.17, 128.39, 129.64, 130.65, 131.17, 144.94, 146.48, 148.84, 152.18, 157.24, 165.97, 166.83.

EXAMPLE 34

Reaction of 36 with PEG diamine hydrochloride (13)- Bis-Camptothecin-NPEG$_{40kDa}$-20-O-Glycinate— Compound 37a Continuing to refer to FIG. 11, a solution of PEG$_{40kDa}$ diamine hydrochloride (13, 5 g, 0.125 mmol), 20-Iodoacetyl camptothecin (36, 322 mg, 0.624 mmol) and triethylamine (208 μL, 1.497 m.mol) in anhydrous methylene chloride (75 mL) were stirred at room temperature for 3 days. The solvent was evaporated under reduced pressure and the solid obtained was recrystallized from DMF followed by 2-propanol to give 37a as a white solid(4.4 g,87.4%).

EXAMPLE 35

Reaction of Compound 37a with acetic anhydride-Bis-Camptothecin-N-Acetyl-PEG$_{40kDa}$-20-O-Glycinate— Compound 37b Continuing to refer to FIG. 11, the preparation of the N-acetyl derivative of 37a is illustrated and designated 37b. A solution of compound 37a (300 mg, 0.007 m.mol), acetic anhydride (28 μL) and pyridine (28 μL) in anhydrous methylene chloride (5 mL) was stirred at room temperature for 18 hours. The solvent was removed and the residue was crystallized from 2-propanol to give 200 mg of 37b.

EXAMPLE 36

Reaction of 36 with PEG N-methyldiamine hydrochloride (12)—Compound 38

Also shown in FIG. 11, a solution of PEG$_{40kDa}$ N-methyldiamine hydrochloride (12, 5 g, 0.125 mmol), 20-Iodoacetyl camptothecin (36, 322 mg, 0.624 mmol) and triethylamine (208 μL, 1.497 m.mol) in anhydrous methylene chloride (75 mL) were stirred at room temperature for 3 days. The solvent was evaporated under reduced pressure and the solid obtained was recrystallized from DMF followed by 2-propanol to give 38 as a white solid (4.5 g,90%).

EXAMPLE 37

20-Sarcosine Camptothecin (41)

Figure 12:
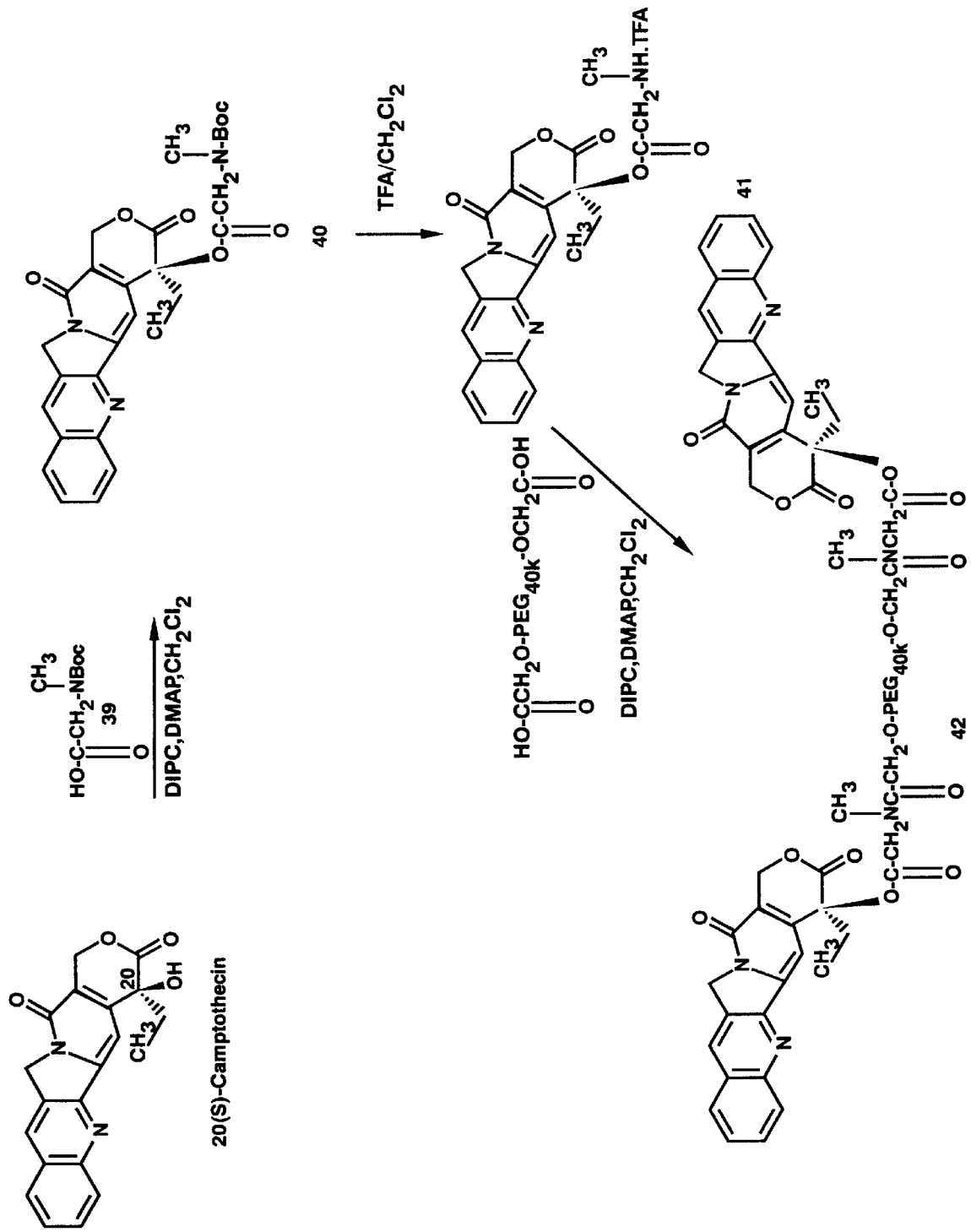

Referring now to FIG. 12, a mixture of Sarcosine (5 g, 56.13 mmol), Boc anhydride (14.7 g, 67.35 m.mol) and sodium hydroxide (4.5 g, 112.26 m.mol) in water (25 mL) was stirred at room temperature for 18 hours. The reaction mixture was cooled to 0° C. and was acidified to pH 3 with 6N HCl and extracted with ethyl acetate. Evaporation of the solvent gave Boc Sarcosine, 39, as a clear oil.

$^1$H NMR (CDCl$_3$) δ 4.58(m),3.0(s)4.0(m).

Boc-Sarcosine (39, 1.63 g,8.61 mmol) was dissolved in 100 mL of anhydrous methylene chloride at room temperature and to this solution at 0° C. were added DIPC (1.3 mL, 8.61 mmol), DMAP (725 mg, 5.74 mmol) and camptothecin (1 g, 2.87 mmol) at 0° C. The reaction mixture was allowed to warm to room temperature and left for 2 hours. The solution was washed with 0.1N HCl, dried and evaporated under reduced pressure to yield a white solid which was recrystallized from 2-propanol to give 20-Boc-sarcosine camptothecin (40, 750 mg, 50.3%).

20-Boc-sarcosine camptothecin (40, 750 mg) was dissolved in methylene chloride (4 ml) and trifluoroaceticacid (4 ml) and stirred at room temperature for 1 hour. Ether (10 ml) was added and the precipitated solid was filtered and dried to give 41 (550 mg, 85%) as yellow solid.

$^1$H NMR(DMSO)δ1.0(t), 2.2(m), 2.7 (s), 2.84(s), 4.4–4.6 (dd), 5.11 (brs), 5.34(s), 5.65(s), 7.36(s), 7.6–8.3(m), 8.74 (s), 9.46(s).

$^{13}$C NMR (DMSO)δ 7.55, 30.21, 32.49, 47.87, 50.22, 66.40, 77.72, 95.34, 118.84, 127.74, 127.95, 128.76, 129.67, 130.51, 131.65, 144.64, 147.88, 152.24, 156.48, 158.23, 166.78.

EXAMPLE 38

Reaction of 41 with PEG dicarboxylic acid—Compound 42

Continuing to refer to FIG. 12, PEG$_{40kDa}$ diacid (2 g, 0.05 mmol) was dissolved in 30 mL of anhydrous methylene chloride at room temperature and to this solution at 0° C. were added DIPC (30 μL, 0.20 mmol), DMAP (24 mg, 0.20 mmol) and 20-sarcosine camptothecin (41, 112 mg, 0.21 mmol). The reaction mixture was allowed to warm to room temperature and left for 16 hours. The solution was evaporated under reduced pressure to yield a white solid which was recrystallized from 2-propanol to give 42 (1.4 g,69%).

EXAMPLE 39 a) PEG$_{40kDa}$Glycine (50)

PEG$_{40kDa}$ diacid (9.5 g, 0.23 mmol) was dissolved in 20 mL of anhyd. methylene chloride at room temperature and to this solution at 0° C. were added DIPC (141 μL, 0.92 mmol), DMAP (197 mg, 1.6 mmol) and glycine-t-butylester (176.4 mg, 0.92 mmol) at 0° C. The reaction mixture was allowed to warm to room temperature after 3 hours and left for 16 hours. The solution was washed with 0.1N HCl, dried and evaporated under reduced pressure to yield PEG$_{40kDa}$glycine t-butyl ester as a white solid which was dissolved in a mixture of methylene chloride (50 ml) and trifluoroaceticacid (25 ml )at 0° C. for overnight. Solvent was removed and the solid was recrystallized from methylene chlorideIether to give 50 (7.1 g, 75%). $^{13}$C NMR (CDCl$_3$)δ 39.42, 69.59, 70.19, 169.39, 169.46.

b) PEG$_{40kDa}$phenylalanine (51)

PEG$_{40kDa}$ diacid (9.5 g, 0.23 mmol) was dissolved in 20 mL of anhyd. methylene chloride at room temperature and to this solution at 0° C. were added DIPC (141 μL, 0.92 mmol), DMAP (197 mg, 1.6 mmnol) and phenylalanine-t-butyl ester (176.4 mg, 0.92 mmol) at 0° C. The reaction mixture was allowed to warm to room temperature after 3 hours and left for 16 hours. The solution was washed with 0.1N HCl, dried and evaporated under reduced pressure to yield PEG$_{40kDa}$phenylalanine t-butyl ester as a white solid which was dissolved in a mixture of methylene chloride (50 ml) and trifluoroaceticacid (25 ml) at 0° C. for overnight. Solvent was removed and the solid was recrystallized from methylene chloride/ether to give 51 (7.1 g, 75%).

$^{13}$C NMR (CDCl$_3$)δ 39.42, 69.59, 70.19, 169.39, 169.46.

c) PEG$_{40kDa}$leucine (52)

PEG$_{40kDa}$ diacid (9.5 g, 0.23 mmol) was dissolved in 20 mL of anhyd. methylene chloride at room temperature and to this solution at 0° C. were added DIPC (141 μL, 0.92 mmol), DMAP (197 mg, 1.6 mmol) and leucine-t-butyl ester(176.4 mg, 0.92 mmol) at 0° C. The reaction mixture was allowed to warm to room temperature after 3 hours and left for 16 hours. The solution was washed with 0.1N HCl, dried and evaporated under reduced pressure to yield PEG$_{40kDa}$leucine t-butyl ester as a white solid which was dissolved in a mixture of methylene chloride (50 ml )and trifluoroaceticacid (25 ml ) at 0° C. for overnight. Solvent was removed and the solid was recrystallized from methylene chloride/ether to give 52 (7.1 g, 75%). $^{13}$CNMR (CDCl$_3$)δ 39.42, 69.59, 70.19, 169.39, 169.46.

d) PEG$_{40kDa}$Proline (53)

PEG$_{40kDa}$ diacid (9.5 g, 0.23 mmol) was dissolved in 20 mL of anhyd. methylene chloride at room temperature and to this solution at 0° C. were added DIPC (141 μL, 0.92 mmol), DMAP (197 mg, 1.6 mmol) and proline-t-butylester (176.4 mg, 0.92 mmol) at 0° C. The reaction mixture was allowed to warm to room temperature after 3 hours and left for 16 hours. The solution was washed with 0.1N HCl, dried and evaporated under reduced pressure to yield PEG$_{40kDa}$proline t-butyl ester as a white solid which was dissolved in a mixture of methylene chloride(50 ml)and trifluoroaceticacid (25 ml )at 0° C. for overnight. Solvent was removed and the solid was recrystallized from methylene chloride/ether to give 53 (7.1 g,75%). $^{13}$C NMR (CDCl$_3$)δ39.42, 69.59, 70.19, 169.39, 169.46.

e) PEG$_{40kDa}$methionine (54)

PEG$_{40kDa}$ diacid (9.5 g, 0.23 mmol) was dissolved in 20 mL of anhyd. methylene chloride at room temperature and to this solution at 0° C. were added DIPC (141 μL, 0.92 mmol), DMAP (197 mg, 1.6 mmol) and meththionine-t-butylester (176.4 mg, 0.92 mmol) at 0° C. The reaction mixture was allowed to warm to room temperature after 3 hours and left for 16 hours. The solution was washed with 0.1N HCl, dried and evaporated under reduced pressure to yield PEG$_{40kDa}$ methionine t-butyl ester as a white solid which was dissolved in a mixture of methylene chloride (50 ml) and trifluoroaceticacid (25 ml )at 0° C. for overnight. Solvent was removed and the solid was recrystallized from methylene chloride/ether to give 54 (7.1 g,75%). $^{13}$C NMR (CDCl$_3$)δ 39.42, 69.59, 70.19, 169.39, 169.46.

EXAMPLE 40

Acyclovir-PEG prodrug

PEG$_{40kDa}$L-alanine diacid (29, 11.5 g, 0.287 mmol) is dissolved in 200 mL of anhydrous methylene chloride at room temperature and to this solution at 0° C. are added DIPC (0.175 ml, 1.15 mmol μL), DMAP (140 mg, 1.15 mmol) and acyclovir (258 mg, 1.15 mmol). The reaction mixture is allowed to warm to room temperature after 2 hours and left for 16 hours. The solution is concentrated to about 100 ml and filtered through celite and the filterate is evaporated under reduced pressure to yield acyclovir-PEG prodrug as a solid which is recrystallized from CH$_2$Cl$_2$/ether.

EXAMPLE 41

CyclosporinA-PEG prodrug

PEG$_{40kDa}$glycine diacid (50, 11.5 g, 0.287 mmolg,) is dissolved in 200 mL of anhydrous methylene chloride at room temperature and to this solution at 0° C. are added DIPC (0.175 ml, 1.15 mmol μL), DMAP (140 mg, 1.15 mmol) and cyclosporin A (1.3 g, 1.15 mmol). The reaction mixture is allowed to warm to room temperature after 2 hours and left for 16 hours. The solution is concentrated to about 100 ml and filtered through celite and the filterate is evaporated under reduced pressure to yield cyclosporin A-PEG prodrug as a solid which is recrystallized from CH$_2$Cl$_2$/ether.

EXAMPLE 42

Amoxicillin-PEG prodrug

PEG$_{40kDa}$phenylalanine diacid (51, 11.5 g, 0.287 mmol) is dissolved in 200 mL of anhydrous methylene chloride at room temperature and to this solution at 0° C. are added DIPC (0.175 ml, 1.15 mmol μL), DMAP (140 mg, 1.15 mmol) and amoxicillin (419 mg, 1.15 mmol). The reaction mixture is allowed to warm to room temperature after 2 hours and left for 16 hours. The solution is concentrated to about 100 ml and filtered through celite and the filterate is evaporated under reduced pressure to yield amoxicillin-PEG prodrug as a solid which is recrystallized from CH$_2$Cl$_2$/ether.

EXAMPLE 43

Fluconazole-PEG prodrug

PEG$_{40kDa}$leucine diacid (52, 11.5 g, 0.287 mmol) is dissolved in 200 mL of anhydrous methylene chloride at room temperature and to this solution are added DIPC (0.175 ml, 1.15 mmol μL), DMAP (140 mg,1.15 mmol) and fluconazole (352 mg, 1.15 mmol) at 0° C. The reaction mixture is allowed to warm to room temperature after 2 hours and left for 16 hours. The solution is concentrated to about 100 ml and filtered through celite and the filterate is evaporated under reduced pressure to yield fluconazole-PEG prodrug as a solid which is recrystallized from CH$_2$Cl$_2$/ether.

EXAMPLE 44

Floxuridine-PEG prodrug

PEG$_{40kDa}$proline diacid (53, 0.5 g, 0.0125 mmol,) is dissolved in 20 mL of anhydrous methylene chloride at room temperature and to this solution are added 2-chloro-1-methylpyridinium iodide (17 mg, 0.067 mmol), DMAP (17 mg, 0.14 mmol) and floxuridine (13 mg, 0.049 mmol) at 0° C. The reaction mixture is allowed to warm to room temperature after 2 hours and left for 16 hours. The solution is concentrated to about 100 ml and filtered through celite and the filterate is evaporated under reduced pressure to yield floxuridine-PEG prodrug as a solid which is recrystallized from CH$_2$Cl$_2$/ether.

EXAMPLE 45

IN VITRO BIOASSAY

In this example, a series of in vitro assays were conducted to determine the $IC_{50}$ for unmodified camptothecin, unmodified paclitaxel and several of the high molecular weight prodrugs prepared as set forth above.

All compounds were independently tested against one or more of the P388/O (murine lymphoid neoplasm, Southern Research Institute), HT-29 (human colon carcinoma) and A549 (human lung adeno carcinoma) cell lines.

The P388/O cells were grown in RPMI 1640 medium (Whittaker Bioproducts, Walkersville, Md.)+10% FBS (Hyclone Inc., Logan, Utah). The HT-29 cells were grown in DMEM (GIBCOBRL)+10% FBS (Eyclone, Inc.). The A549 cells were grown in DMEM/F-12 (Biowhitaker)+10% FBS (Heat inactivated). Bioassays were performed in their respective media containing antibiotics and fungizone.

Camptothecin and paclitaxel were dissolved in DMSO and diluted to the appropriate concentration in culture media. The PEG-Camptothecin and PEG-paclitaxel prodrugs were dissolved in water and diluted to the appropriate concentrations in culture media.

The assays were performed in duplicate in 96-well microtiter cell culture plates. Two fold serial dilution of the compounds were done in the microtiter plates. Cells were detached by incubating with 0.1% Trypsin/Versene at 37°. Trypsin was inactivated by adding the appropriate media for each cell line containing 10% FBS. To each well of the microtiter plates, 10,000 cells were added. After three days, cell growth was measured by addition of a metabolic indicator dye, Alamar Blue, according to the manufacturer's protocol. The $IC_{50}$ value for each test compound was determined and compared to the $IC_{50}$ for the appropriate reference compound.

| | $IC_{50}$ (nM) | |
|---|---|---|
| Compound # | P388 | HT-29 |
| Camptothecin | 5 | 21 |
| Topotecan | 29 | 99 |
| 5a | 7 | 30 |
| 5b | 18 | 153 |
| 31 | 98 | 305 |
| 37a | 24 | 110 |
| 37b | 49 | 137 |
| 42 | 15 | 46 |
| 45 | 9 | 27 |
| 49 | 33 | 40 |

P-388—Murine leukemia cell line
HT-29—Human colon carcinoma cell line

Referring now to the table, it can be seen that the relatively high molecular weight polymer prodrugs compare favorably to unmodified forms of the drug.

EXAMPLE 46

IN VIVO STUDY

In this Example, the in vivo activity of some of the compounds prepared in accordance with the present invention was assessed using the Murine Leukemia Model and the Colorectal Xenograft model.

Murine Leukemia Model (In vivo P388)

The compounds shown in the Table below were screened for in vivo activity against the murine leukemia cell line P388/O (mouse, lymphoid neoplasm). The cell line was obtained from Southern Research Institute (Birmingham, Ala.) and grown in RPMI 1640 supplemented with 10% FBS. P388/O cells were subcultured two times per week and log phase cultures (viability $\geq 95\%$) were used for all in vivo experiments. Female CD2F1 mice (Taconic Farms, Germantown, N.Y.) at 7–8 weeks of age were used for study. Following one week of acclimation, mice were implanted ip with P388/O cells ($5 \times 10^5$ cells/mouse) at designated day 0 (zero). The mice were randomly assigned to experimental groups (10–20 per group). The groups included Control groups and several which received one of the drugs or prodrugs. The mice were then dosed (500 µL, ip) for 5 consecutive days (days 1–5). Control groups received vehicle (intralipid or water). The mice were monitored for up to 40 days, and the treatment was evaluated and expressed as the percentage survival at 40 days.

Colorectal Xenograft (In vivo HT-29)

Female nu/nu mice (Harlan Sprague Dawley, Madison, Wis.), 18–24 g and 10–14 weeks old, at onset of treatment were used. The solid tumor HT-29 (human, colon adenocarcinoma) was obtained from the ATCC (HTB 38) and grown in DMEM supplemented with 10% FBS. Cells were subcultured once a week and for in vivo experiments viabilities were $\geq 90\%$. Mice were housed in microisolator filtration racks, and maintained with filtered acidified water and sterile laboratory chow ad libitum. Following one week of acclimation, tumors were established by injecting $1 \times 10^6$ harvested HT-29 tumor cells in a single subcutaneous site, on the flank of mice in the left axillary region. The tumor injection site was observed twice weekly and measured once palpable. The tumor volume for each mouse was determined by measuring two dimensions with calipers and calculated using the formula: tumor volume=(length×width$^2$)/2. When tumors reached the average volume of 300 mm$^3$, the mice were divided into their experimental groups. The non-Control groups received Camptothecin 2.5 mg/kg/day, the prodrugs being dosed on the basis of camptotbecin content. The mice were sorted to evenly distribute tumor size, grouped into 5 mice/cage, and ear punched for permanent identification. Mice receiving drugs were treated i.p. 5 times a week, Monday through Friday for 5 weeks with 500 µL of test article. Mouse weight and tumor size were measured at the beginning of study and weekly through week 7. The overall growth of tumors was expressed as the percent change in tumor size calculated by subtracting mean initial tumor volume from mean tumor volume at the end of the treatment and dividing by mean initial tumor volume. Thus, any tumor group which did not respond to treatment and grew over the course of the experiment would display a zero or positive percent change and treatment groups in which tumors regressed would exhibit a negative percent change.

The resulting data are presented below:

| | P388 data | | |
|---|---|---|---|
| Compound # | total active dose mg/kg | 50% survival (days) | Survival Rate % |
| Control-untreated | 0 | 13 | NA |
| Camptothecin | 16 | NA | 80 |
| Camptothecin-20-O-ester of PEG$_{20kDa}$ diacid | 11.4 | 21 | 10 |
| Compound 15 (PEG$_{40kDa}$) | 16 | NA | 60 |
| Compound 48 (PEG$_{40kDa}$) | 16 | NA | 80 |

The data in this Table illustrates that cure rate obtained using the prodrugs of the present invention was comparable to that of the unmodified or native camptothecin compound. Furthermore, groups treated with each of the prodrug compositions exceeded the 50% survival time of the untreated group. In addition, the survival rate of the higher molecular weight compounds was approximately the same as that with the unmodified camptothecin.

| Compound # | Total active dose (mg/kg) | Tumor growth (%) | Body weight change (%) | Mortality (%) |
|---|---|---|---|---|
| HT-29 data | | | | |
| WEEK 5 (end of treatment) | | | | |
| Control | NA | 723 | +6 | 100 |
| Campto-thecin | 62.5 | −20 | −3 | 50 |
| 15 | 62.5 | −60 | 1 | 30 |
| 48 | 62.5 | −80 | −9 | 0 |
| WEEK 7 (2 week post treatment) | | | | |
| Control | NA | 1347 | +8 | |
| Campto-thecin | 62.5 | 62 | −3 | |
| 15 | 62.5 | −73 | +13 | |
| 48 | 62.5 | −96 | +25 | |

In addition to the increased water solubility provided by the prodrug formulations of the present invention, the data indicates that the PEG-prodrug compounds are more efficacious and less toxic than parent compounds. Of particular interest are the facts that even 2 weeks after treatment was ceased, the animals treated with the prodrugs still exhibited decreases in tumor volume and the animals had body weight gains comparable to the control animals. While Applicants are not bound by theory, it is believed that the unique combination of higher molecular weight polymer and the controlled rate of hydrolysis of the particular ester linkages allow therapeutic amounts of the parent compound to be generated before the prodrug is cleared from the body. It is also concluded that the prodrug compositions accumulated to a certain degree in the tumor areas and provided a localized and residual effect.

EXAMPLE 47

Preparation of camptothecin-20-O-carbonylimidazolylcarbonate (54)

In a 100 mL round bottomed flask were placed camptothecin 1 (1 g, 2.88 mmol), N,N-carbonyldiimidazole (2.335 g, 14.4 mmol) and methylene chloride (50 mL), stirred for 10 minutes, followed by the addition of dimethylaminopyridine (110 mg, 0.864 mmol). The resulting clear solution was stirred at room temperature under a nitrogen atmosphere for 4 hours. The reaction mixture was diluted with 50 mL of methylene chloride, washed with 50 mL of 0.1N HCl, followed by 50 mL of water. The organic layer was dried over anhydrous magnesium sulfate, and evaporated to dryness. The crude product thus obtained (604 mg, 95%) was used without further purification for the preparation of camptothecin 20-O-carbamate derivatives. $^{13}$C NMR (67.8 MHz, CDCl$_3$)δ:166.21, 157.07, 151.91, 148.75, 147.12, 146.83, 144.40, 137.10, 131.20, 131.09, 130.71, 129.466, 128.33, 128.10, 120.11, 117.17, 95.13, 78.93, 67.17, 49.98, 31.82, 7.62. $^1$H NMR (270 MHz, CDCl$_3$)δ: 8.41 (s, 1), 8.22 (s, 1), 8.20 (d, 1), 7.95 (d, 1), 7.83 (t, 1), 7.67 (t, 1), 7.46 (s, 1), 7.25 (s, 1), 7.13 (s, 1), 5.62 (d of d, 2), 5.32 (s, 2), 2.38 (m, 2), 1.10 (t, 3).

EXAMPLE 48

Preparation of camptothecin-20-O-para nitrophenyl carbonate (55)

In a 100 mL round bottomed flask were placed camptothecin 1 (0.5 g, 1.44 mmol), paranitrophenylchloroformate (0.871 g, 4.3 mmol) and methylene chloride (15 mL), stirred for 30 minutes at −8° C., followed by the addition of dimethylaminopyridine (1.06 g, 8.61 mmol). The resulting clear solution was stirred at room temperature under a nitrogen atmosphere for 2 hours. The precipitated solid was filtered and dried to give the product The filtrate was diluted with 25 mL of methylene chloride, washed with 10 mL of 0.1N HCl, followed by 10 mL of 0.1N sodium bicarbonate solution. The organic layer was concentrated to 5 mL and precipitated with ether and over anhydrous, magnesium sulfate, and evaporated to dryness to give additional quantity of the product. Total yield of the product (604 mg, 95%). $^{13}$C NMR (67.8 MHz, CDCl$_3$)δ:166.80, 157.18, 155.05, 152.17, 151.23, 148.93, 146.83, 145.60, 144.82, 131.31, 130.86, 129.59, 128.46, 128.25, 125.25, 121.70, 120.40, 95.47, 79.32, 67.21, 50.05, 31.92, 7.64.
$^1$H NMR (270 MHz, CDCl$_3$)δ:8.43 (s, 1), 8.25 (d, 1), 8.22 (d, 2), 7.96 (d, 1), 7.86 (t, 1), 7.70 (t, 1), 7.40 (d, 2), 7.38 (s, 1), 5.57 (d of d, 2), 5.31 (s, 2), 2.31 (m, 2), 1.07 (t, 3).

EXAMPLE 49

Preparation of camptothecin- 20-O-N-hydroxysuccinimidyl carbonate (56)

In a 50 mL round bottomed flask were placed camptothecin 1 (100 mg, 0.288 mmol), disuccinimidyl carbonate (0.369 mg, 1.44 mmnol) and methylene chloride (7 mL), stirred for 5 minutes, followed by the addition of dimethylaminopyridine (110 mg, 0.864 mmol). The resulting clear solution was stirred at room temperature under a nitrogen atmosphere for 2 days. The reaction mixture was diluted with 50 mL of methylene chloride, washed with 25 mL of 0.1N HCl, followed by 25 mL of water. The organic layer was dried over anhydrous, magnesium sulfate, and evaporated to dryness to give the product (60 mg, 95%).$^{13}$C NMR (67.8 MHz, CDCl$_3$)δ: 168.53, 167.77, 160.28, 157.18, 153.00, 151.00, 149.04, 144.03, 131.05, 130.63, 130.01, 128.38, 128.23, 128.13, 120.50, 95.68, 80.88, 67.04, 50.08, 31.85, 20.17, 7.64. $^1$HNMR (270 MHz, CDCl$_3$)δ: 8.40 (s, 1), 8.29 (d, 1), 7.92 (d, 1), 7.84 (t, 1), 7.67 (t, 1), 7.45 (s, 1), 5.53 (d of d, 2), 5.30 (s, 2), 3.10 (t, 4), 2.32 (in 2), 1.05 (t, 3).

EXAMPLE 50a

Preparation of camptothecin-20-O-PEG carbamates (57)

A solution of 54 (176 mg, 0.4 mmol), and PEG 40 kDa NH$_2$ (4 g, 0.1 mmol) in anhydrous 2-propanol (75 mL) and dimethylaminopyridine (37 mg, 0.3 mmol) was refluxed for 21 hours. The reaction mixture was cooled to room temperature and the separated solid was filtered and washed with ether. The solid obtained was recrystallized from 2-propanol (80 mL) twice to give 3.67 g of product. $^{13}$C NMR (67.8 MHz, CDCl$_3$)δ: 172.0, 162.0, 155.0, 153.0, 149.0, 145.0, 144.0, 134.0, 133.5, 133.0, 132.0, 129.5, 128.5, 127.5, 97.5, 88.5, 68.03, 58.5, 50.00, 39.95, 32.0, 7.0.

EXAMPLE 50b

Preparation of camptothecin-20-O-PEG-5000 carbamate

The process of Example 50a described supra was repeated except that PEG-5000 was used in place of PEG 40 kDa NH$_2$. The T$_{1/2}$ in rat plasma for this compound was determined to be 7.5 hours.

EXAMPLE 51a

Preparation of camptothecin-20-O-PEG 40 kDa carbonate (58)

In a 25 ml round bottomed flask under nitrogen atmosphere were placed camptothecin (228 mg, 0.65 mmol ), PEG 40 kDa OH (4 g, 0.1 mmol) and 5 mL of anhydrous methylene chloride. To this solution were added triphosgene (72 mg, 0.24 mmol) and dimethylaminopyridine (243 mg, 1.9 mmol) and stirring continued for 16 hours. The reaction mixture was filtered through celite and evaporated to dryness. The solid obtained was crystallized from 2-propanol. $^{13}$C NMR(67.8 MHz, CDCl$_3$)

EXAMPLE 51b

Preparation of camptothecin-20-O-PEG-5000 carbonate

The process of Example 51a described supra was repeated except that PEG-5000 was used in place of PEG 40 kDa NH$_2$.

EXAMPLE 52

Preparation of camptothecin-20-O-methylcarbonate (59)

A solution of 55 (500 mg, 0.976 mmol), in anhydrous methanol (15 mL), and methylene chloride (15 mL) and dimethylaminopyridine (60 mg, 0.488 mmol) was stirred at room temperature for 2 hours. The reaction mixture was washed with 3 mL of 0.1N HCl, followed by 3 mL of 0.1N sodium bicarbonate solution, dried (anhydrous magnesium sulfate) and evaporated to a small volume (5 mL) followed by the addition of ether to precipitate the product. The solid obtained was filtered and dried to give 59 (0.395 g, 83%) $^{13}$C NMR (67.8 MHz, CDCl$_3$)δ: 167.06, 157.44, 154.34, 152.64, 149.25, 146.57, 145.94, 130.92, 130.58, 129.95, 128.65, 128.38, 128.13, 128.02, 120.77, 95.97, 77.96, 67.12, 55.32, 50.00, 31.19, 7.54. $^1$H NMR (270 MHz, CDCl$_3$)δ: 8.41 (s, 1), 8.24 (d, 1), 7.96 (d, 1), 7.85 (t, 1), 7.68 (t, 1), 7.34 (s, 1), 5.56 (d of d, 2), 5.30 (s, 2), 3.79 (s, 3), 2.23 (m, 2), 1.01 (t, 3).

EXAMPLE 53

Preparation of camptothecin-20-O-isobutyryl carbonate (60).

To a solution of camptothecin (500 mg, 1.44 mmol) and dimethylaminopyridine (1.5 mg, 0.012 mmol) in anhydrous methylene chloride (25 mL), was added isobutyryl chloroformate and the contents were stirred at room temperature for 2 hours. The reaction mixture was washed with 3 mL of 0.1N HCl, followed by 3 mL of 0.1N sodium bicarbonate solution, dried (anhydrous magnesium sulfate) and evaporated to give the product. $^{13}$C NMR (67.8 MHz, CDCl$_3$)δ: 167.19, 157.44, 153.92, 152.62, 149.22, 146.49, 146.12, 130.92, 130.57, 129.93, 128.64, 128.35, 128.13, 128.00, 120.67, 96.01, 75.05, 67.09, 49.98, 31.13, 27.86, 18.75, 7.59.

$^1$H NMR (270 MHz, CDCl$_3$)δ: 8.40 (s, 1), 8.23 (d, 1), 7.95 (d, 1), 7.84 (t, 1), 7.67 (t, 1), 7.35 (s, 1), 5.55 (d of d, 2), 5.29 (s, 2), 3.90 (m, 2), 2.24 (m, 2), 1.98 (m, 1), 1.01 (t, 3), 0.94 (d, 6).

EXAMPLE 54

The IC$_{50}$ values for some of the compounds formed in examples 47–53 were determined using the same process as that described above with regard to example 45 and compared to native camptothecin. The results are provided below.

| Compound # | Description | IC$_{50}$ (nM) |
|---|---|---|
|  | camptothecin | 7 |
| 54 | camptothecin-20-O-carbonylimidazolyl carbonate | 69 |
| 55 | camptothecin-20-O-paranitrophenyl carbonate | 365 |
| 56 | camptothecin-20-O-N-hydroxysuccinimidyl carbonate | 1030 |
| 57 | camptothecin-20-O-PEG5kDa carbamate | 912 |
| 59 | camptothecin-20-O-methyl carbonate | 11 |
| 60 | camptothecin-20-O-isobutyryl carbonate | 29 |

The various publications, patents, patent applications and published applications mentioned in this application are hereby incorporated by reference herein.

We claim:

1. A composition comprising the formula:

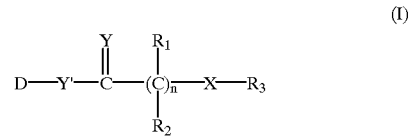

(I)

wherein:
D is a residue of biologically active moiety;
X is an electron withdrawing group;
Y and Y' are independently O or S;
(n) is zero (0) or a positive integer;
R$_1$ and R$_2$ are independently selected from the group consisting of H, C$_{1-6}$ alkyls, aryls, substituted aryls, aralkyls, heteroalkyls, substituted heteroalkyls and substituted C$_{1-6}$ alkyls;
R$_3$ is a substantially non-antigenic polymer, C$_{1-12}$ straight or branched alkyl or substituted alkyl, C$_{5-8}$ cycloalkyl or substituted cycloalkyl, carboxyalkyl, carboalkoxy alkyl, dialkylaminoalkyl, phenylalkyl, phenylaryl or

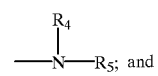

R$_4$ and R$_5$ are independently selected from the group consisting of H, C$_{1-6}$ alkyls, aryls, substituted aryls, aralkyls, heteroalkyls, substituted heteroalkyls, and substituted C$_{1-6}$ alkyls or jointly form a cyclic C$_5$–C$_7$ ring.

2. The composition of claim 1, wherein R$_3$ is a substantially non-antigenic polymer having a capping group Z.

3. The composition of claim 2, wherein Z is selected from the group consisting of OH, C$_{1-4}$ alkyl moieties, or

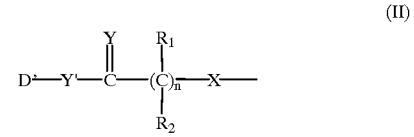

(II)

wherein D' is selected from the group consisting of D, biologically active moieties other than D, dialkyl ureas, C$_{1-4}$ alkyls and carboxylic acids.

4. The composition of claim 1, wherein R$_1$ and R$_2$ are independently H, methyl or ethyl.

5. The composition of claim 1, wherein said substituted C$_{1-6}$ alkyl is selected from the group consisting of carboxyalkyls, aminoalkyls, dialkylaminos, hydroxyalkyls, and mercaptoalkyls.

6. The composition of claim 1, wherein X is selected from the group consisting of O, N(R$_1$), S, SO and SO$_2$.

7. The composition of claim 1, wherein X is selected from the group consisting of O and N(R$_1$).

8. The composition of claim 1, wherein (n) is zero (0), 1, or 2.

9. The composition of claim 1, wherein Y and Y' are O.

10. The composition of claim 1, wherein R$_3$ comprises a polyalkylene oxide.

11. The composition of claim 10, wherein said polyalkylene oxide comprises polyethylene glycol.

12. The composition of claim 10, wherein said polyalkylene oxide has a molecular weight of from about 20,000 to about 80,000.

13. The composition of claim 10, wherein said polyalkylene oxide has a molecular weight of from about 25,000 to about 45,000.

14. The composition of claim 13, wherein said polyalkylene oxide has a molecular weight of from about 30,000 to about 42,000.

15. The composition of claim 11, wherein R$_3$ is selected from the group consisting of:

—C(Y)—(CH$_2$)$_n$—(CH$_2$CH$_2$O)$_x$—R"; —C(Y)—Y—(CH$_2$)$_n$—(CH$_2$CH$_2$O)$_x$—R";

—C(Y)—NR$_1$—(CH$_2$)$_n$—(CH$_2$CH$_2$O)$_x$—R"; and —CHR$_1$—(CH$_2$)$_n$—(CH$_2$CH$_2$O)$_x$—R";

wherein

R$_1$ is independently selected from the group consisting of H, C$_{1-6}$ alkyls, aryls, substituted aryls, aralkyls, heteroalkyls, substituted heteroalkyls and substituted C$_{1-6}$ alkyls;

(n) is zero (0) or is a positive integer;

Y is O or S;

R" is a capping group or R$_1$; and (x) represents the degree of polymerization.

16. A composition of claim 1 having the formula:

wherein R$_1$ is H or CH$_3$; and
X is O or S.

17. The composition of claim 1, wherein D is selected from the group consisting of paclitaxel, taxotere, camptothecin and podophyllotoxin.

18. The composition of claim 1, wherein D is a member of the group consisting of paclitaxel and taxotere and Y' is attached to the 2' position of said paclitaxel, taxane or taxotere residues.

19. The composition of claim 17, wherein D is a camptothecin derivative residue and Y' is attached to the 20S position of said camptothecin derivative.

20. The composition of claim 1, wherein D is a residue selected from the group consisting of biologically active proteins, enzymes, peptides, anti-tumor agents, cardiovascular agents, anti-neoplastics, anti-infectives, anti-fungals, anti-anxiety agents, gastrointestinal agents, central nervous system-activating agents, analgesics, fertility agents, contraceptive agents, anti-inflammatory agents, steroidal agents, anti-urecemic agents, vasodilating agents, and vasoconstricting agents.

21. A method of treating mammals with prodrugs, comprising:
administering to a mammal in need of such treatment an effective amount of a composition of claim 1.

22. A method of preparing a polymer-based prodrug having a circulation half-life greater than its in-vivo hydrolysis half-life, comprising:
reacting a biologically active moiety containing an available hydroxyl group with a bifunctional spacer moiety containing an available carboxylic acid group in the presence of a first coupling agent to form a biologically active moiety—spacer prodrug intermediate,
reacting said biologically active moiety—spacer prodrug intermediate with a substantially non-antigenic polymer containing a terminal group selected from the group consisting of carboxylic acid, amine and hydroxyl in the presence of a second coupling agent and recovering the polymer-based prodrug.

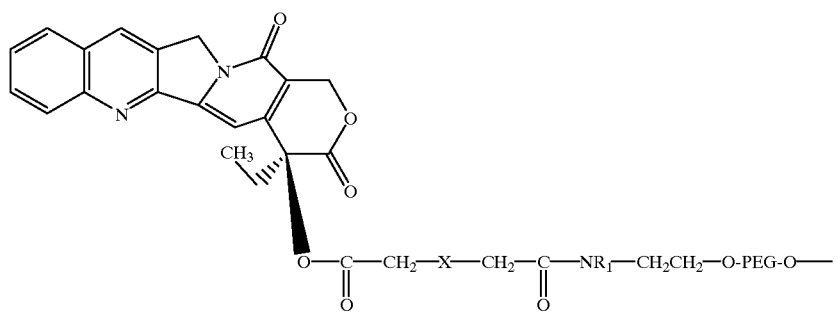

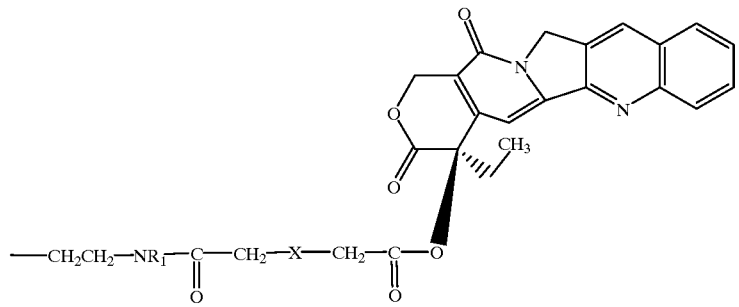

23. The method of claim 22, wherein said biologically active moiety is selected from the group consisting of biologically active proteins, enzymes, peptides, anti-tumor agents, cardiovascular agents, anti-neoplastics, anti-infectives, anti-fungals, anti-anxiety agents, gastrointestinal agents, central nervous system-activating agents, analgesics, fertility agents, contraceptive agents, anti-inflammatory agents, steroidal agents, anti-urecemic agents, vasodilating agents, and vasoconstricting agents.

24. The method of claim 22, wherein said bifunctional spacer moiety is selected from the group consisting of diglycolic acid, thiodiglycolic acid, l-alanine, d-alanine, hydroxyacetic acid and bromoacetic acid.

25. The method of claim 22, wherein said first and said second coupling agents are independently selected from the group consisting of 1,3-diisopropylcarbodiimide (DIPC), dialkyl carbodiimides, 2-halo-1-alkyl-pyridinium halides, 1-(3-dimethylaminopropyl)-3-ethyl carbodiimide (EDC), propane phosphonic acid cyclic anhydride (PPACA) and carbodiimide (CDI).

26. The method of claim 22, wherein said substantially non-antigenic polymer containing a terminal carboxylic acid group or a terminal amine group comprises a polyalkylene oxide.

27. The method of claim 26, wherein said polyalkylene oxide has a molecular weight of from about 20,000 to about 80,000.

28. A method of preparing a biologically active nucleophile conjugate, comprising:

contacting a biologically active nucleophile with a compound of the formula:

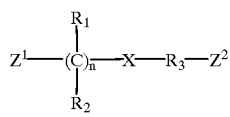

wherein:

X is an electron withdrawing group;

Y and Y' are independently O or S;

(n) is zero (0) or a positive integer;

$R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;

$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

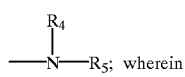 wherein $R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring;

$Z^1$ and $Z^2$ are independently $CO_2H$, $CO_2R_6$, $OR_7$, $CONR_1R_8$, H, a $C_{1-4}$ alkyl

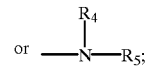

where $R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring;

$R_6$ is $R_4$ or an N-hydroxysuccinimide, an N-hydroxybenzotriazole, an N-acyl thazolidine, imidazole or an acid activating group;

$R_7$ is $R_4$ or C(O)-halogen, para nitrophenyl carbonate, imidazolyl carbonate, or N-hydroxysuccinimidyl carbonate; and $R_8$ is $R_4$ or $CR_1R_2CO_2H$;

and recovering the resultant biologically active nucleophile conjugate.

29. A method of forming a camptothecin-based conjugate, comprising:

1) forming a camptothecin derivative containing bifunctional spacer containing moiety, by contacting said camptothecin derivative with a bifunctional spacer containing moiety in the presence of a coupling agent;

2) forming the trihaloacetic acid deriviative of said camptothecin derivative containing said bifunctional spacer containing moiety; and 3) reacting said trihaloacetic acid derivative of said camptothecin derivative containing said bifunctional spacer containing moiety with a diacid derivative of a substantially non-antigenic polymer.

30. A compound comprising the formula:

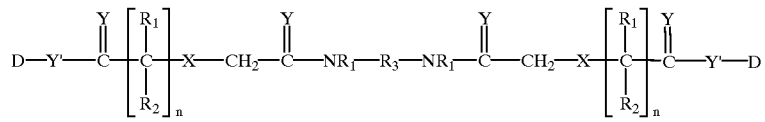

wherein:

D is a residue of biologically active moiety;

X is an electron withdrawing group;

Y and Y' are independently O or S;

(n) is zero (0) or a positive integer;

$R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;

$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

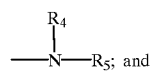

$R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring.

31. The compound of claim 30, wherein $R_1$ and $R_2$ are H.

32. The compound of claim 30, wherein $R_3$ comprises a polyalkylene oxide.

33. The compound of claim 32, wherein said polyalkylene oxide comprises polyethylene glycol.

34. The compound of claim 32, wherein said polyalkylene oxide has a molecular weight of from about 20,000 to about 80,000.

35. The compound of claim 30 having the formula:

wherein all variables are as set forth above.

36. The compound of formula 30, wherein D is a residue of an anti-fungal agent.

37. The compound of formula 35, wherein D is a residue of an anti-fungal agent.

38. A method of preparing prodrugs, comprising:

reacting an amino acid ester of a hydroxy-containing biologically-active moiety with a carboxylic acid of a substantially non-antigenic polymer derivative or a carboxylic acid derivative of a substantially non-antigenic polymer in the presence of a coupling agent.

39. The method of claim 38, wherein said amino acid ester of a hydroxy-containing biologically-active moiety is a 20-O-amino acid ester of a camptothecin derivative.

40. The method of claim 39, wherein said 20-O-amino acid ester of camptothecin is selected form the group consisting of camptothecin-20-O-(l)-alanate, camptothecin-20-O-(d)-alanate and racemic mixtures thereof.

41. The method of claim 38, wherein said coupling agent is 1,3-diisopropylcarbodiimide (DIPC).

42. The method of claim 38, wherein said hydroxy-containing biologically-active moiety is a hydroxyl-containing anti-fungal agent.

43. A compound comprising the formula:

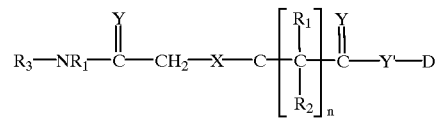

D is a residue of biologically active moiety;

X is an electron withdrawing group;

Y and Y' are independently O or S;

(n) is zero (0) or a positive integer;

$R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;

$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

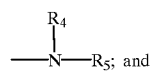

$R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring.

44. The compound of claim 43, wherein $R_1$ and $R_2$ are H and X is O.

45. The compound of claim 44, wherein $R_3$ comprises a polyalkylene oxide.

46. The compound of claim 45, wherein said polyalkylene oxide comprises polyethylene glycol.

47. The compound of claim 46, wherein said polyalkylene oxide has a molecular weight of from about 20,000 to about 80,000.

48. The compound of claim 43, wherein D is a residue of a hydroxyl-containing anti-fungal agent.

49. A compound comprising the formula:

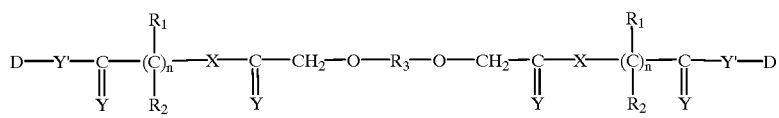

wherein:

D is a residue of biologically active moiety;

X is an electron with drawing group;

Y and Y' are independently O or S;

(n) is zero or a positive integer;

$R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;

$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

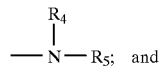

$R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring.

50. The compound of claim 49, wherein D is a residue of a hydroxyl-containing anti-fungal agent and X is NH.

51. A compound comprising the formula:

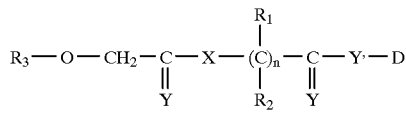

wherein:

D is a residue of biologically active moiety;

X is an electron with drawing group;

Y and Y' are independently O or S;

(n) is zero or a positive integer;

$R_1$ and $R_2$ are selected from the group consisting of H, $C_{1-6}$ alkyls, aryls, substituted aryls, aralkyls, heteroalkyls, substituted heteroalkyls and substituted $C_{1-6}$ alkyls;

$R_3$ is a substantially non-antigenic polymer, $C_{1-12}$ straight or branched alkyl or substituted alkyl, $C_{5-8}$ cycloalkyl or substituted cycloalkyl, carboxyalkyl, carboalkoxy alkyl, dialkylaminoalkyl, phenylalkyl, phenylaryl or

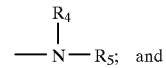

$R_4$ and $R_5$ are independently selected from the group consisting of H, $C_{1-6}$ alkyls, aryls, substituted aryls, aralkyls, heteroalkyls, substituted heteroalkyls, and substituted $C_{1-6}$ alkyls or jointly form a cyclic $C_5$–$C_7$ ring.

52. The compound of claim 51, wherein D is a residue of a hydroxyl-containing anti-fungal agent and X is NH.

* * * * *

UNITED STATES PATENT AND TRADEMARK OFFICE
CERTIFICATE OF CORRECTION

PATENT NO. : 5,965,566
DATED : October 12, 1999
INVENTOR(S) : GREENWALD, R.B., et al.

It is certified that error appears in the above-identified patent and that said Letters Patent is hereby corrected as shown below:

Title page item [57] Abstract, line 5: after "residue of" insert --a--;

Column 3, line 21: after "residue of" insert --a--;
Column 34, line 27: after "residue of" insert --a--;
Column 36, line 10: change "20S" to --20 S--.
Column 38, line 60: after "residue of" insert --a--;
Column 40, line 10: after "residue of" insert --a--;
Column 41, line 2: after "residue of" insert --a--;
Column 42, line 2: after "residue of" insert --a--;

Signed and Sealed this

Twentieth Day of February, 2001

Attest:

NICHOLAS P. GODICI

*Attesting Officer*  *Acting Director of the United States Patent and Trademark Office*